United States Patent [19]
Hohlweg et al.

[11] Patent Number: 6,133,268
[45] Date of Patent: Oct. 17, 2000

[54] 1,4-DISUBSTITUTED PIPERAZINES

[75] Inventors: Rolf Hohlweg, Kvistgaard; Peter Madsen, Bagsvaerd; Tine Krogh Jørgensen, Herlev; Knud Erik Andersen, Smørum; Brett Watson, Værløse, all of Denmark; Zdenek Polivka, Praha, Czech Rep.; Otylie Konigova, Praha, Czech Rep.; Martina Kovandova, Praha, Czech Rep.; Alexandra Silhánková, Praha, Czech Rep.; Vladimir Valenta, Praha, Czech Rep.

[73] Assignee: Novo Nordisk A/S, Bagsvaerd, Denmark

[21] Appl. No.: 09/271,564

[22] Filed: Mar. 18, 1999

Related U.S. Application Data

[62] Division of application No. 09/943,726, Oct. 3, 1997, Pat. No. 5,916,889.

[30] Foreign Application Priority Data

Oct. 4, 1996 [DK] Denmark ................... 1090/96

[51] Int. Cl.[7] .................. A61K 31/496; C07D 401/04; C07D 295/073; C07D 295/155
[52] U.S. Cl. .................. 514/252.14; 514/253.01; 514/253.12; 514/253.13; 514/254.01; 514/255.03; 544/295; 544/360; 544/372; 544/380
[58] Field of Search .................. 544/360, 380, 544/372, 295; 514/252, 252.14, 253.01, 253.12, 253.13, 254.01, 255.03

[56] References Cited

U.S. PATENT DOCUMENTS

| | | | |
|---|---|---|---|
| 3,435,073 | 3/1969 | Mequon et al. .................. | 544/380 |
| 3,436,391 | 4/1969 | Holm .................. | 544/380 |
| 4,835,156 | 5/1989 | Cirera et al. .................. | 544/380 |
| 4,994,463 | 2/1991 | Oshima et al. .................. | 514/253 |
| 5,422,351 | 6/1995 | Piwinski et al. .................. | 544/360 |

FOREIGN PATENT DOCUMENTS

| | | |
|---|---|---|
| 132764 | 2/1985 | European Pat. Off. |
| WO 95/18793 | of 0000 | WIPO . |
| WO 96/31498 | of 0000 | WIPO . |

OTHER PUBLICATIONS

Plilai et al, Indian J. Chem., vol. 14B, p. 714–716 (1976).
Sindelar et al., Collection Czech. Chem. Commun., vol. 59, pp. 667–674 (1994).

Primary Examiner—Emily Bernhardt
Attorney, Agent, or Firm—Steve T. Zelson; Carol E. Rozek

[57] ABSTRACT

The present invention relates to 1,4-disubstituted piperazines of the general formula

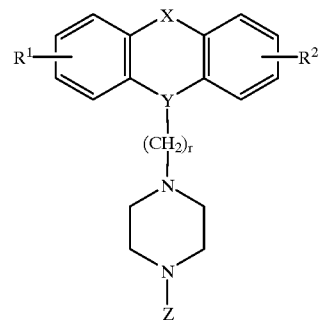

wherein X, Y, Z, $R^1$, $R^2$ and r are as defined in the detailed part of the present description or salts thereof, to methods for their preparation, to compositions containing them, and to their use for the clinical treatment of painful, hyperalgesic and/or inflammatory conditions in which C-fibers play a pathophysiological role by eliciting neurogenic pain or inflammation as well as their use for the treatment of indications caused by or related to the secretion and circulation of insulin antagonising peptides, e.g. non-insulin-dependent diabetes mellitus (NIDDM) and ageing-associated obesity.

27 Claims, No Drawings

1,4-DISUBSTITUTED PIPERAZINES

CROSS-REFERENCE TO RELATED APPLICATIONS

This application is a divisional of application Ser. No. 08/943,726 filed Oct. 3, 1997, now U.S. Pat. No. 5,916,889 and claims priority under 35 U.S.C. 119 of Danish application 1090/96 filed Oct. 4, 1996, the contents of which are fully incorporated herein by reference.

FIELD OF INVENTION

The present invention relates to novel N-substituted azaheterocyclic compounds in which a substituted alkyl chain forms part of the N-substituent or salts thereof, to methods for their preparation, to compositions containing them, to the use of the compounds for preparing compositions for the clinical treatment of painful, hyperalgesic and/or inflammatory conditions in which C-fibres play a pathophysiological role by eliciting neurogenic pain or inflammation, and to methods of treating said painful, hyperalgesic and/or inflammatory conditions. The invention also relates to the use of the present compounds for reducing blood glucose and/or inhibit the secretion, circulation or effect of insulin antagonising peptides like CGRP or amylin, the present compounds being known to interfere with neuropeptide containing C-fibres. Hence the present compounds can be used in the treatment of insulin resistance in non-insulin-dependent diabetes mellitus (NIDDM) in order to improve the glucose tolerance as well as ageing-associated obesity.

BACKGROUND OF INVENTION

The nervous system exerts a profound effect on the inflammatory response. Antidromic stimulation of sensory nerves results in localised vasodilation and increased vascular permeability (Janecso et al. Br. J. Pharmacol. 1967, 31, 138–151) and a similar response is observed following injection of peptides known to be present in sensory nerves. From this and other data it is postulated that peptides released from sensory nerve endings mediate many inflammatory responses in tissues like skin, joint, urinary tract, eye, meninges, gastro-intestinal and respiratory tracts. Hence inhibition of sensory nerve peptide release and/or activity, may be useful in treatment of, for example arthritis, dermatitis, rhinitis, asthma, cystitis, gingivitis, thrombophlelitis, glaucoma, gastro-intestinal diseases or migraine.

Further, the potent effects of CGRP on skeletal muscle glycogen synthase activity and muscle glucose metabolism, together with the notion that this peptide is released from the neuromuscular junction by nerve excitation, suggest that CGRP may play a physiological role in skeletal muscle glucose metabolism by directing the phosphorylated glucose away from glycogen storage and into the glycolytic and oxidative pathways (Rossetti et al. Am. J. Physiol. 264, E1–E10, 1993). This peptide may represent an important physiological modulator of intracellular glucose trafficking in physiological conditions, such as exercise, and may also contribute to the decreased insulin action and skeletal muscle glycogen synthase in pathophysiological conditions like NIDDM or ageing-associated obesity (Melnyk et al. Obesity Res. 3, 337–344, 1995) where circulating plasma levels of CGRP are markedly increased. Hence inhibition of release and/or activity of the neuropeptide CGRP may be useful in the treatment of insulin resistance related to type 2 diabetes or ageing.

In U.S. Pat. Nos. 4,383,999 and 4,514,414 and in EP 236342 as well as in EP 231996 some derivatives of N-(4,4-disubstituted-3-butenyl)azaheterocyclic carboxylic acids are claimed as inhibitors of GABA uptake. In EP 342635 and EP 374801, N-substituted azaheterocyclic carboxylic acids in which an oxime ether group and vinyl ether group forms part of the N-substituent respectively are claimed as inhibitors of GABA uptake. Further, in WO 9107389 and WO 9220658, N-substituted azacyclic carboxylic acids are claimed as GABA uptake inhibitors. EP 221572 claims that 1-aryloxyalkylpyridine-3-carboxylic acids are inhibitors of GABA uptake.

SUMMARY OF THE INVENTION

The present invention relates to compounds of the general formula 1, wherein X, Y, Z, $M_1$, $M_2$, $R^1$ through $R^{12}$, r and m are as defined in the detailed part of the present description.

The present compounds are useful for the treatment, prevention, elimination, alleviation or amelioration of an indication related to all painful, hyperalgesic and/or inflammatory conditions in which C-fibres play a pathophysiological role, e.g. neurogenic pain, inflammation, migraine, neuropathy, itching and rheumatoid arthritis, as well as indications caused by or related to the secretion and circulation of insulin antagonising peptides, e.g. non-insulin-dependent diabetes mellitus (NIDDM) and ageing-associated obesity.

In another aspect, the present invention includes within its scope pharmaceutical compositions comprising, as an active ingredient, at least one of the compounds of the general formula I or a pharmaceutically acceptable salt thereof together with a pharmaceutically acceptable carrier or diluent.

In another aspect of the present invention there is provided a method of treating painful, hyperalgesic and/or inflammatory conditions in which C-fibres play a pathophysiological role, e.g. neurogenic pain, inflammation, migraine, neuropathy, itching and rheumatoid arthritis, as well as a method of treating indications caused by or related to the secretion and circulation of insulin antagonising peptides like CGRP or amylin, e.g. non-insulin-dependent diabetes mellitus (NIDDM) and ageing-associated obesity. The method of treating may be described as the treatment of one of the above indications in a subject in need thereof, which comprises the step of administering to the said subject a neurologically effective amount of a compound of the invention, or a pharmaceutically acceptable salt thereof.

A further aspect of the invention relates to the use of a compound of the present invention for the preparation of a pharmaceutical composition for the treatment of all painful, hyperalgesic and/or inflammatory conditions in which C-fibres play a pathophysiological role, e.g. neurogenic pain, inflammation, migraine, neuropathy, itching and rheumatoid arthritis, as well as for the treatment of indications caused by or related to the secretion and circulation of insulin antagonising peptides, e.g. non-insulin-dependent diabetes mellitus (NIDDM) and ageing-associated obesity.

Further objects will become apparent from the following description.

DETAILED DESCRIPTION OF THE INVENTION

Accordingly, the present invention relates to novel 1,4-disubstituted piperazines of formula I:

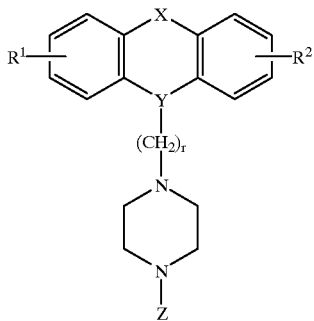

(I)

wherein R¹ and R² independently are hydrogen, halogen, trifluoromethyl, hydroxy, $C_{1-6}$-alkyl or $C_{1-6}$-alkoxy; and X is ortho-phenylene, —O—, —S—, —C($R^6R^7$)—, —CH₂CH₂—, —CH=CH—CH₂—, —CH₂CH=CH—, —CH₂—(C=O)—, —(C=O)—CH₂—, —CH₂CH₂CH₂—, —CH=CH—, —N($R^8$)—(C=O)—, —(C=O)—N($R^8$)—, —O—CH₂—, —CH₂—O—, —OCH₂O—, —S—CH₂—, —CH₂—S—, —(CH₂)N($R^8$)—, —N($R^8$)(CH₂)—, —N(CH₃)SO₂—, —SO₂N(CH₃)—, CH($R^{10}$)CH₂—, —CH₂CH($R^{10}$), —(C=O)—, —N($R^9$)— or —(S=O)— wherein $R^6$, $R^7$, $R^8$ and $R^9$ independently are hydrogen or $C_{1-6}$-alkyl; and wherein $R^{10}$ is $C_{1-6}$-alkyl or phenyl; and Y is >N—CH₂—, >CH—CH₂—, >C=CH—, >CH—O— wherein only the underscored atom participates in the ring system; and r is 1, 2 or 3; and Z is selected from

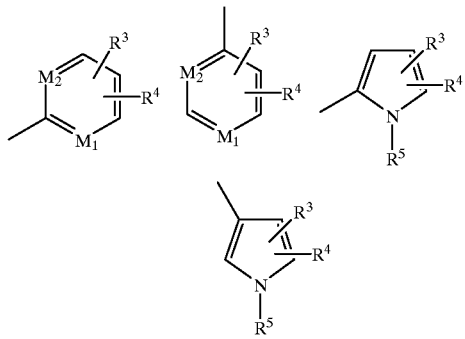

wherein M₁ and M₂ independently are CH or N; and

R⁵ is hydrogen, $C_{1-6}$-alkyl, phenyl or benzyl; and

R³ is hydrogen, halogen, trifluoromethyl, nitro or cyano; and

R⁴ is hydrogen, halogen, trifluoromethyl, nitro, cyano, (CH₂)$_m$COR¹¹, (CH₂)$_m$OH or (CH₂)$_m$SO₂R¹¹ wherein R¹¹ is hydroxy, $C_{1-6}$-alkoxy or NHR¹², wherein R¹² is hydrogen or $C_{1-6}$-alkyl; and m is 0, 1, or 2; or R⁴ is selected from

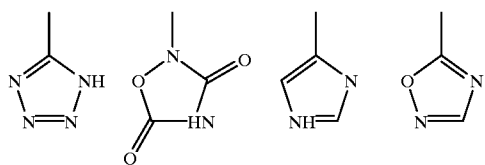

-continued

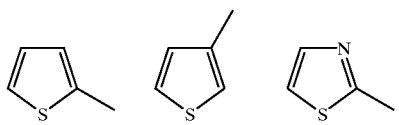

or a pharmaceutically acceptable salt thereof.

The compounds of formula I may exist as geometric and optical isomers and all isomers, as separated, pure or partially purified stereoisomers or racemic mixtures thereof are included in the scope of the invention. Isomers may be separated by means of standard methods such as chromatographic techniques or fractional crystallisation of suitable salts.

Preferably, the compounds of formula I exist as the individual geometric or optical isomers.

The compounds according to the invention may optionally exist as pharmaceutically acceptable acid addition salts or—when the carboxylic acid group is not esterified—as pharmaceutically acceptable metal salts or—optionally alkylated—ammonium salts.

Examples of such salts include inorganic and organic acid addition salts such as hydrochloride, hydrobromide, sulphate, phosphate, acetate, fumarate, maleate, citrate, lactate, tartrate, oxalate or similar pharmaceutically acceptable inorganic or organic acid addition salts, and include the pharmaceutically acceptable salts listed in Journal of Pharmaceutical Science, 66, 2 (1977) which are known to the skilled artisan.

Also included are the hydrates of the above mentioned acid addition salts which the present compounds are able to form.

The acid addition salts may be obtained as the direct products of compound synthesis. In the alternative, the free base may be dissolved in a suitable solvent containing the appropriate acid, and the salt isolated by evaporating the solvent or by precipitation or crystallisation.

The compounds of formula I may be administered in a pharmaceutically acceptable acid addition salt form or where possible as a metal or a lower alkylammonium salt. Such salt forms exhibit approximately the same order of activity as the free base forms.

In the above structural formula and throughout the present specification, the following terms have the indicated meaning:

The term "$C_{1-6}$-alkyl" as used herein, alone or in combination, refers to a straight or branched, saturated hydrocarbon chain having 1 to 6 carbon atoms such as e.g. methyl, ethyl, n-propyl, isopropyl, n-butyl, sec-butyl, isobutyl, tert-butyl, n-pentyl, 2-methylbutyl, 3-methylbutyl, 4-methylpentyl, neopentyl, n-hexyl, 1,2-dimethylpropyl, 2,2-dimethylpropyl and 1,2,2-trimethylpropyl.

The term "$C_{1-6}$-alkoxy" as used herein, alone or in combination, refers to a straight or branched monovalent substituent comprising a $C_{1-6}$-alkyl group linked through an ether oxygen having its free valence bond from the ether oxygen and having 1 to 6 carbon atoms e.g. methoxy, ethoxy, propoxy, isopropoxy, butoxy, pentoxy.

The term "halogen" means fluorine, chlorine, bromine or iodine.

In a preferred embodiment of the invention R¹ and R² are selected from hydrogen halogen, trifluoromethyl or $C_{1-6}$-alkyl. Preferably R¹ and R² are hydrogen, halogen or methyl.

In a another preferred embodiment of the invention X is selected from —CH₂CH₂—, —CH=CH—, —O—CH₂—, —CH$_2$—O—, —OCH$_2$O—, —S—CH$_2$— or —CH$_2$—S—. Preferably X is selected from —CH$_2$CH$_2$—, —OCH$_2$O—, —S—CH$_2$— or —CH$_2$—S—.

In another preferred embodiment of the invention Y is selected from >N—CH$_2$—, >C=CH— or >CH—O— wherein only the underscored atom participates in the ring system.

In another preferred embodiment of the invention r is 1 or 2.

In another preferred embodiment of the invention Z is selected from

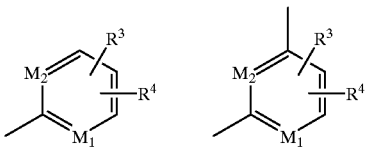

wherein M$_1$ and M$_2$ independently are CH or N.

In another preferred embodiment of the invention R$^3$ is hydrogen, trifluoromethyl, nitro or cyano.

In another preferred embodiment of the invention R$^4$ is hydrogen, trifluoromethyl, nitro, cyano or (CH$_2$)$_m$COR$^{11}$.

In another preferred embodiment of the invention m is 0 or 1.

In yet another preferred embodiment of the invention R$^{11}$ is hydroxy.

Preferred compounds of the present invention include:

2-(4-(3-(12H-Dibenzo[d,g][1,3]dioxocin-12-ylidene)-1-propyl)piperazin-1-yl)-3-pyridinecarboxylic acid, 2-(4-(3-(2,10-Dichloro-12H-dibenzo[d,g][1,3]dioxocin-12-ylidene)-1-propyl)-piperazin-1-yl)-3-pyridinecarboxylic acid, 2-(4-(3-(12H-Dibenzo[d,g][1,3,6]dioxazocin-12-yl)-1-propyl)piperazin-1-yl)-3-pyridinecarboxylic acid, 2-(4-(3-(2-Chloro-12H-dibenzo[d,g][1,3,6]dioxazocin-12-yl)-1-propyl)-piperazin-1-yl)-3-pyridinecarboxylic acid, 1-(3-(10,11-Dihydro-5H-dibenzo[a,d]cyclohepten-5-ylidene)-1-propyl)-4-(2-pyridyl)piperazine, 2-(4-(3-(10,11-Dihydro-5H-dibenzo[a,d]cyclohepten-5-ylidene)-propyl)-1-piperazinyl)-3-pyridine-carboxylic acid, 2-(4-(2-(10,11-Dihydro-5H-dibenz[b,f]azepin-5-yl)-1-ethyl)-1-piperazinyl)-3-pyridinecarboxylic acid, 6-(4-(3-(10,11-Dihydro-5H-dibenz[b,f]azepin-5-yl)-1-propyl)-1-piperazinyl)-2-pyridinecarboxylic acid, 2-(4-(3-(10,11-Dihydro-5H-dibenz[b,f]azepin-5-yl)-1-propyl)-1-piperazinyl)-3-pyridinecarboxylic acid, 2-(4-(3-(10,11-Dihydro-5H-dibenzo[b,f]azepin-5-yl)-1-propyl)-1-piperazinyl)-5-pyridinecarboxylic acid, 2-(4-(3-(3-Chloro-10,11-dihydro-5H-dibenzo[b,f]azepin-5-yl)-1-propyl)-1-piperazinyl)3-pyridinecarboxylic acid, 1-(3-(10,11-Dihydro-5H-dibenzo[a,d]cyclohepten-5-ylidene)-1-propyl)-4-(2-nitrophenyl)-piperazine, 2-(4-(3-(10,11-Dihydro-5H-dibenzo[a,d]cyclohepten-5-ylidene)-1-propyl)-1-piperazinyl)benzonitrile, 2-(4-(3-(10,11-Dihydro-5H-dibenzo[a,d]cyclohepten-5-ylidene)-1-propyl)-1-piperazinyl)-benzoic acid, 1-(3-(10,11-Dihydro-5H-dibenzo[a,d]cyclohepten-5-ylidene)-1-propyl)-4-(3-trifluoromethyl-2-pyridyl) piperazine, 2-(4-(2-(6,11-Dihydro-dibenzo[b,e]thiepin-11-ylidene) ethyl)piperazin-1-yl)-3-pyridinecarboxylic acid, 2-(4-(3-(6,11-Dihydrodibenzo[b,e]thiepin-11-ylidene)-1-propyl)-1-piperazinyl)-3-pyridinecarboxylic acid, 2-(4-(2-(6,11-Dihydrodibenzo[b,e]thiepin-11-yloxy)ethyl)-1-piperazinyl)-3-pyridinecarboxylic acid, 6-(4-(3-(10,11-Dihydro-5H-dibenzo[a,d]cyclohepten-5-ylidene)-1-propyl)piperazin-1-yl)-2-pyridinecarboxylic acid, 2-(4-(3-(3-Methyl-10,11-dihydro-5H-dibenzo[b,f]azepin-5-yl)-1-propyl)-1-piperazinyl)-3-pyridinecarboxylic acid, 6-(4-(3-(Dibenzo[d,g][1,3,6]dioxazocin-12-yl)-1-propyl)-piperazin-1-yl)-pyridine-2-carboxylic acid, or a pharmaceutically acceptable salt thereof.

It has been demonstrated that the novel compounds of formula I inhibit neurogenic inflammation which involves the release of neuropeptides from peripheral and central endings of sensory C-fibres. Experimentally this can be demonstrated in animal models of histamine induced paw oedema (Europ. J. Pharmacol. 279, 227–231, 1995) in which the novel compounds of formula I exhibit a potent inhibitory effect. Compounds of formula I may be used to treat all painful, hyperalgesic and/or inflammatory conditions in which C-fibres play a pathophysiological role by eliciting neurogenic pain or inflammation, i.e.:

Acutely painful conditions exemplified by migraine, post-operative pain, burns, bruises, post-herpetic pain (Zoster) and pain as it is generally associated with acute inflammation; chronic, painful and/or inflammatory conditions exemplified by various types of neuropathy (diabetic, post-traumatic, toxic), neuralgia, rheumatoid arthritis, spondylitis, gout, inflammatory bowel disease, prostatitis, cancer pain, chronic headache, coughing, asthma, itching, chronic pancreatitis, inflammatory skin disease including psoriasis and autoimmune dermatoses, osteoporotic pain.

Further, it has been demonstrated that the compounds of general formula I improve the glucose tolerance in diabetic ob/ob mice and that this may result from the reduced release of CGRP from peripheral nervous endings. Hence the compounds of general formula I may be used in the treatment of NIDDM as well as ageing-associated obesity. Experimentally this has been demonstrated by the subcutaneous administration of glucose into ob/ob mice with or without previous oral treatment with a compound of general formula I.

The compounds of formula I may be prepared by the following method:

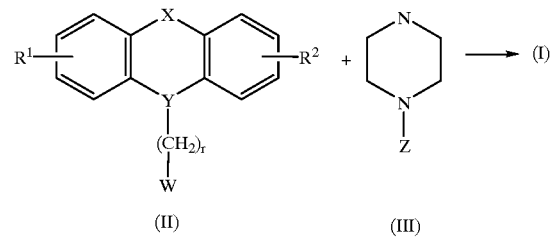

A compound of formula II wherein R$^1$, R$^2$, X, Y and r are as defined above and W is a suitable leaving group such as halogen, p-toluene sulphonate or mesylate may be reacted with an aza compound of formula III wherein Z is as defined above. This alkylation reaction may be carried out in a solvent such as acetone, dibutylether, 2-butanone, methyl ethyl ketone, ethyl acetate, tetrahydrofuran (THF) or toluene in the presence of a base e.g. sodium hydride and a catalyst, e.g. an alkali metal iodide at a temperature up to reflux temperature for the solvent used for e.g. 1 to 120 h. If esters have been prepared in which R$^{11}$ is alkoxy, compounds of formula I wherein R$^{11}$ is OH may be prepared by hydrolysis of the ester group, preferably at room temperature in a mixture of an aqueous alkali metal hydroxide solution and an alcohol such as methanol or ethanol, for example, for about 0.5 to 6 h.

Compounds of formula II and III may readily be prepared by methods familiar to those skilled in the art.

Under certain circumstances it may be necessary to protect the intermediates used in the above methods e.g. a compound of formula III with suitable protecting groups. The carboxylic acid group can, for example, be esterified. Introduction and removal of such groups is described in "Protective Groups in Organic Chemistry" J. F. W. McOrnie ed. (New York, 1973).

Pharmacological Methods

I. Histamine Induced Paw Oedema

The rat histamine paw oedema test was performed essentially as described by Amann et al. (Europ. J. Pharmacol. 279, 227–231, 1995). In brief 250–300 g male Sprague-Dawley rats were anaesthetized with pentobarbital sodium, and placed on a 32 degree (Celsius) heated table. Ten minutes later histamine (50 micoliter, 3 mg/ml) was injected in the right hind paw and 20 minutes hereafter the paw swelling was determined by water plethysmography (Ugo Basile). Test compounds were administered intraperitoneally at 15 minutes before the anaesthetics.

II. Reduced Release of CGRP ob/ob female mice, 16 weeks of age, where injected glucose (2 g/kg) subcutaneously. At times hereafter blood glucose was determined in tail venous blood by the glucose oxidase method. At the end of the study the animals were decapitated and trunk blood collected. Immunoreactive CGRP was determined in plasma by radio-immuno-assay. Two groups of animals were used. The one group was vehicle treated, whereas the other group received a compound of formula I via drinking water (100 mg/l) for five days before the test.

Values for inhibition of histamine induced oedema response for some representative compounds are recorded in table 1.

TABLE 1

Inhibition of histamin induced pain response at 1.0 mg/kg

| Example no. | % Oedema inhibition |
|---|---|
| 2 | 24 |
| 8 | 61 |

Pharmaceutical Compositions

The present invention also relates to pharmaceutical compositions comprising a compound of formula I or a pharmaceutically acceptable salt thereof and, usually, such compositions also contain a pharmaceutical carrier or diluent. The compositions containing the compounds of this invention may be prepared by conventional techniques and appear in conventional forms, for example capsules, tablets, solutions or suspensions.

The pharmaceutical carrier employed may be a conventional solid or liquid carrier. Examples of solid carriers are lactose, terra alba, sucrose, talc, gelatine, agar, pectin, acacia, magnesium stearate and stearic acid. Examples of liquid carriers are syrup, peanut oil, olive oil and water.

Similarly, the carrier or diluent may include any time delay material known to the art, such as glyceryl monostearate or glyceryl distearate, alone or mixed with a wax.

The route of administration may be any route which effectively transports the active compound to the appropriate or desired site of action, such as oral, nasal, pulmonary or parenteral e.g. rectal, depot, transdermal, subcutaneous, intranasal, intramuscular, topical, intravenous, intraurethral, ophthalmic solution or an ointment, the oral route being preferred.

If a solid carrier for oral administration is used, the preparation can be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

For nasal administration, the preparation may contain a compound of formula I dissolved or suspended in a liquid carrier, in particular an aqueous carrier, for aerosol application. The carrier may contain additives such as solubilising agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques contains

| Core: | | |
|---|---|---|
| Active compound (as free compound or salt thereof) | | 100 mg |
| Colloidal silicon dioxide (Areosil ®) | | 1.5 mg |
| Cellulose, microcryst. (Avicel ®) | | 70 mg |
| Modified cellulose gum (Ac-Di-Sol ®) | | 7.5 mg |
| Magnesium stearate | | |
| Coating: | | |
| HPMC | approx. | 9 mg |
| Mywacett ® 9-40 T | approx. | 0.9 mg |

*Acylated monoglyceride used as plasticizer for film coating.

Acylated monoglyceride used as plasticizer for film coating.

The compounds of the invention may be administered to a mammal, especially a human, in need of such treatment, prevention, elimination, alleviation, or amelioration of an indication related to all painful, hyperalgesic and/or inflammatory conditions in which C-fibres play a pathophysiological role such as e.g. neurogenic pain, inflammation, migraine, neuropathy, itching and rheumatoid arthritis, as well as indications caused by or related to the secretion and circulation of insulin antagonising peptides, such as non-insulin-dependent diabetes mellitus (NIDDM) or ageing-associated obesity. Such mammals include also animals, both domestic animals, e.g. household pets, and non-domestic animals such as wildlife.

The compounds of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount.

For the above indications the dosage will vary depending on the compound of formula I employed, on the mode of administration and on the therapy desired. However, in general, satisfactory results are obtained with a dosage of from about 0.5 mg to about 1000 mg, preferably from about 1 mg to about 500 mg of compounds of formula I, conveniently given from 1 to 5 times daily, optionally in sustained release form. Usually, dosage forms suitable for oral administration comprise from about 0.5 mg to about 1000 mg, preferably from about 1 mg to about 500 mg of the compounds of formula I admixed with a pharmaceutical carrier or diluent.

Suitable dosage ranges varies as indicated above depending as usual upon the exact mode of administration, form in which administered, the indication towards which the administration is directed, the subject involved and the body weight of the subject involved, and the preference and experience of the physician or veterinarian in charge.

Generally, the compounds of this invention are dispensed in unit dosage form comprising 50–200 mg of active ingredient in or together with a pharmaceutically acceptable carrier per unit dosage.

Usually, dosage forms suitable for oral, nasal, pulmonal or transdermal administration comprise from about 0.5 mg to about 1000 mg, preferably from about 1 mg to about 500 mg of the compounds of formula I admixed with a pharmaceutically acceptable carrier or diluent.

Any novel feature or combination of features described herein is considered essential to this invention.

EXAMPLES

The process for preparing compounds of formula I and preparations containing them is further illustrated in the following examples, which, however, are not to be construed as limiting.

Hereinafter, TLC is thin layer chromatography, CDCl₃ is deutero chloroform and DMSO-d₆ is hexadeutero dimethylsulfoxide. The structures of the compounds are confirmed by either elemental analysis or NMR, where peaks assigned to characteristic protons in the title compounds are presented where appropriate. $^1$H NMR shifts ($\delta_H$) are given in parts per million (ppm). M.p. is melting point and is given in ° C. and is not corrected. Column chromatography was carried out using the technique described by W. C. Still et al, J. Org. Chem. (1978), 43, 2923–2925 on Merck silica gel 60 (Art. 9385). Compounds used as starting materials are either known compounds or compounds which can readily be prepared by methods known per se.

Example 1

2-(4-(3-(12H-Dibenzo[d,g][1,3]dioxocin-12-ylidene)-1-propyl)piperazin-1yl)-3-pyridinecarboxylic acid hydrochloride

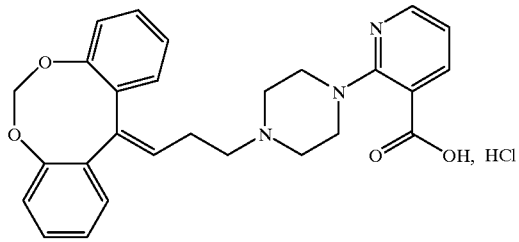

2,2'-Dihydroxybenzophenone (10.0 g, 46.7 mmol) and diiodomethane (13.1 g, 49 mmol) was dissolved in dry N,N-dimethylformamide (180 ml). Dried finely powdered potassium carbonate (9.2 g, 66.7 mmol) was added and the mixture was heated at 105° C. for 16 h. After cooling to room temperature the reaction mixture was poured into ice water (500 ml). The precipitate was collected by filtration after 0.5 h, washed with water on the filter and dissolved in a mixture of ethanol (80 ml) and 4 N sodium hydroxide (20 ml). The solution was stirred at reflux temperature for 1 h, cooled and diluted with water (300 ml). The formed crystalline precipitate was filtered off, washed with water (50 ml) and dried in vacuo, affording 12H-dibenzo[d,g][1,3]dioxocin-12-one as a solid (9.5 g, 90%).

M.p. 93–95° C.

A solution of cyclopropylmagnesium bromide in dry tetrahydrofuran (prepared from cyclopro-pylbromide (24.2 g, 0.2 mol), magnesium turnings (4.86 g, 0.2 mol) and dry tetrahydrofuran (70 ml) was placed under an atmosphere of nitrogen. A solution of the above ketone (9.05 g, 40 mmol) in dry tetrahydrofuran (50 ml) was added dropwise. The reaction mixture was stirred at 40° C. for 1.5 h, cooled and added to an icecold mixture of saturated ammonium chloride (400 ml) and ether (200 ml). The organic layer was separated and the aqueous phase was extracted with ether (50 ml). The combined organic extracts were washed with water (2×100 ml) and brine (50 ml), dried (MgSO₄), evaporated in vacuo and stripped with toluene (2×25 ml). This furnished 11.2 g 12-cyclopropyl-12H-dibenzo[d,g][1,3]dioxocin-12-ol.

$^1$H NMR (200 MHz, CDCl₃): δ0.50 (d, 2H); 0.75 (d, 2H); 2.00 (m, 1H); 5.14 (s, 2H); 6.9–7.4 (m, 6H); 7.81 (d, 2H).

To a solution of the above alcohol (6.21 g, 22 mmol) in dry dichloromethane (225 ml) trimethyl-silylbromosilane (3.71 g, 24.2 mmol) was added. The reaction mixture was stirred at room temperature for 1 h and poured on an icecold saturated sodium hydrogencarbonate solution (75 ml). The organic phase was separated, washed with icewater (2×75 ml) and brine (75 ml), dried (MgSO₄) and evaporated in vacuo. This afforded 7.95 g crude 12-(3-bromo-1-propylidene)-12H-dibenzo[d,g][1,3]dioxocine, which was used in the next step without further purification.

A mixture of the above bromide (5.0 g, 15 mmol), 2-(1-piperazinyl)-3-pyridinecarboxylic acid ethyl ester (3.54 g, 15 mmol, prepared as described in J. Med. Chem. 31, 618–624 (1988)), sodium iodide (2.23 g, 15 mmol) and potassium carbonate (5.1 g, 37 mmol) in 2-butanone (70 ml) was heated at reflux temperature for 5 h. After cooling, the mixture was poured into diethyl ether (170 ml) and water (170 ml). The organic layer was separated, washed with water (2×100 ml), acidified with 2 N hydrochloric acid and washed with water (2×50 ml). The combined aqueous layers were made alkaline using a saturated solution of sodium hydrogen carbonate, and extracted with dichloromethane (200 ml). The organic extract was dried (MgSO$_4$) and evaporated in vacuo. The residue (4.35 g) was purified by chromatography on silica gel using a mixture of benzene and ethyl acetate as eluent to give 2-(4-(3-(12H-dibenzo[d,g][1,3]dioxocin-12-ylidene)-1-propyl)-piperazin-1-yl)-3-pyridinecarboxylic acid ethyl ester (3.71 g, 51%).

A mixture of the above ester (0.99 g, 2 mmol) and 20% sodium hydroxide (1.5 ml) in ethanol (13 ml) was stirred at room temperature for 4 h. The mixture was poured into dichloromethane (100 ml), acidified with 2 N hydrochloric acid and washed with water (10 ml). The organic solution was dried (MgSO$_4$) and activated charcoal was added. The mixture was stirred for 10 minutes, filtered and the solvent was removed in vacuo. The residue was triturated with acetone and the solid product was overlaid with ethyl acetate, stirred for 15 minutes, filtered off and washed with ethyl acetate. After drying, the title compound (0.80 g, 74%) was obtained.

M.p. 225–229° C.

Calculated for $C_{27}H_{27}N_3O_4$, HCl, 0.25 $C_4H_8O_2$, 0.25 $C_2H_5OH$: C, 64.89%; H, 6.02%; Cl, 6.72%; N, 7.96%; Found: C, 64.95%; H, 5.86%; Cl, 6.73%; N, 7.94%.

Example 2

2-(4-(3-(2,10-Dichloro-12H-dibenzo[d,g][1,3]dioxocin-12-ylidene)-1-propyl)-piperazin-1-yl)-3-pyridinecarboxylic acid dihydrochloride

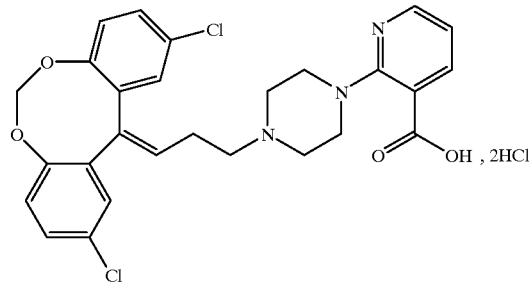

2,2'-Dihydroxy-5,5'-dichlorobenzophenone (12.1 g, 0.042 mol, prepared as described in JACS 77, 543 (1955)) and diiodomethane (11.9 g, 0.044 mol) were dissolved in dry N,N-dimethylformamide (226 ml). Dried and powdered potassium carbonate (8.3 g) was added and the mixture was heated at 105° C. for 5 h and left overnight at room temperature. The reaction mixture was poured on ice (220 g). The precipitate was collected by filtration and dissolved in diethyl ether (500 ml). The organic solution was washed with 5% sodium hydroxide (50 ml), dried (MgSO$_4$) and evaporated in vacuo. This afforded 12 g (96%) of 2,10-dichloro-12H-dibenzo[d,g][1,3]dioxocin-12-one as a solid.

To a solution of cyclopropylmagnesium bromide in dry tetrahydrofuran (prepared from cyclopropylbromide (15.7 g, 0.130 mol), magnesium turnings (3.15 g, 0.130 mol) and dry tetrahydrofuran (45 ml)), a solution of the above ketone (7.65 g, 0.026 mol) in dry tetrahydrofuran (30 ml) was added over 5 minutes under cooling. The reaction mixture was stirred at 38–42° C. for 3 h, cooled in an ice-bath, and a mixture of saturated ammonium chloride (260 ml) and diethyl ether (130 ml) was added. The reaction mixture was then filtered, and the organic layer was separated and the aqueous phase was extracted with diethyl ether (35 ml). The combined organic extracts were washed with water (2×70 ml) and brine (70 ml), dried (MgSO$_4$) and evaporated in vacuo. The crude product was purified by column chromatography on silica gel (140 g) using benzene as eluent. This afforded 8.75 g (98%) of 2,10-dichloro-12-cyclopropyl-12H-dibenzo[d,g][1,3]dioxocin-12-ol as a solid.

To a solution of the above alcohol (8.75 g, 0.027 mol) in dry dichloromethane (245 ml) trimethylsilyl bromide (4.02 g, 0.026 mol) was added. The reaction mixture was stirred at room temperature for 1 h and poured on an ice cold saturated sodium hydrogencarbonate solution (80 ml). The organic phase was separated, washed with water (2×80 ml) and brine (80 ml), dried (MgSO$_4$) and evaporated in vacuo. This afforded 9.12 g of an oil, which was purified by column chromatography on silica gel (250 g) using a mixture of cyclohexane and benzene (3:1) as eluent. This yielded 6.61 g (62%) of 2,10-dichloro-12-(3-bromo-1-propylidene)-12H-dibenzo[d,g][1,3]dioxocine as an oil which crystallized on standing.

A mixture of the above bromide (3 g, 0.008 mol), 2-(1-piperazinyl)-3-pyridinecarboxylic acid ethyl ester (1.76 g, 0.0075 mol), potassium carbonate (3.1 g, 0.022 mol) and sodium iodide (1.1 g, 7.3 mmol) in 2-butanone (35 ml) was heated at reflux temperature for 6 h. After cooling to room temperature, the reaction mixture was diluted with acetone, filtered and evaporated in vacuo. The solid residue was purified by column chromatography on silica gel (100 g) using chloroform as eluent. This afforded 2.7 g (65%) of 2-(4-(3-(2,10-dichloro-12H-dibenzo[d,g][1,3]dioxocin-12-ylidene)-1-propyl)-piperazin-1-yl)-3-pyridinecarboxylic acid ethyl ester as an oil.

The above ester (2.7 g, 4.87 mmol) was dissolved in ethanol (30 ml) and a solution of sodium hydroxide (0.74 g) in water (2.8 ml) was added. The mixture was stirred at room temperature for 48 h. Concentrated hydrochloric acid (2.8 ml) was added followed by dichloromethane (100 ml). The organic layer was separated, dried (MgSO$_4$) and evaporated in vacuo. The resulting foam was stirred with hot acetone (150 ml), the product was filtered off and washed with acetone, affording 1.8 g (62%) of the title compound.

$^1$H NMR (250 MHz, DMSO-d$_6$): $\delta_H$: 8.31 (dd, J=1.9 Hz and 4.7 Hz, 1 H); 8.04 (dd, J=1.9 Hz and 7.5 Hz, 1 H); 7.53 (d, J=2,5 Hz, 1 H); 7.32 (dd, J=2.5 Hz and 8.5 Hz, 1 H); 7.25 (dd, J=2.5 Hz and 8.5 Hz, 1 H); 7.21 (d, J=2.5 Hz, 1 H); 7.10 (d, J=8.5 Hz, 1 H); 6.97 (d, J=8.25 Hz); 6.95 (dd, J=4.7 Hz and 7.5 Hz), S 2 H; 6.15 (t, J=7.5 Hz, 1 H); 5.86 (s, 2 H); 3.73 (bs, 4 H); 3.25 (bt, 6 H); 2.50 (q, J=7.5 Hz, 2 H).

Calculated for $C_{27}H_{25}Cl_2N_3O_4$, 2 HCl, 0.5 H$_2$O: C, 53.30%; H, 4.64%; N, 6.91%; Cl, 23.31%; Found: C, 53.41%; H, 4.60%; N, 6.73%; Cl, 22.71%.

Example 3

2-(4-(3-(12H-Dibenzo[d,g][1,3,6]dioxazocin-12-yl)-1-propyl)piperazin-1-yl)-3-pyridinecarboxylic acid dihydrochloride

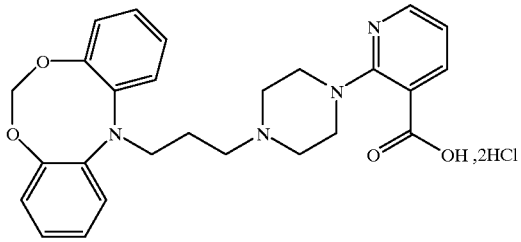

N-(2-Hydroxyphenyl)formamide (16.0 g, 130 mmol) was dissolved in 99.9% ethanol (65 ml). Sodium methoxide (7.0 g, 130 mmol) was suspended in 99.9% ethanol (70 ml) and added dropwise over 30 minutes. The resulting mixture was stirred for 30 minutes. 1-Bromo-2-chloro-methoxybenzene (26.1 g, 118 mmol, synthesis described in J. Heterocycl. Chem., 11, 1974, 331–337) was added dropwise over 15 minutes. The reaction mixture was stirred for 2.5 h at room temperature, heated at reflux temperature for 2 h, and stirred at room temperature overnight. The mixture was filtered and the filtrate evaporated. The residue was dissolved in toluene (500 ml) and washed with a saturated sodium carbonate solution (2×200 ml). The organic phase was dried (MgSO$_4$) and evaporated. The residue was suspended in ethanol (40 ml), filtered and washed with ethanol (3×10 ml). After drying, N-(2-(2-bromophenoxymethoxy)phenyl)formamide (14.1 g, 37%) was obtained.

The above formamide (6.8 g, 21 mmol) was suspended in Dowtherm (75 ml), and potassium carbonate (3.9 g, 28 mmol) was added, followed by copper (1.1 g, 17 mmol) and copper bromide (1.5 g, 11 mmol). The reaction mixture was heated at 180° C. overnight. After cooling, the mixture was filtered, and the filtercake was washed with dichloromethane. Dowtherm and solvent was distilled off, and ethanol (200 ml) was added to the residue, which was left overnight. 4 M Sodium hydroxide (14 ml) was added and the mixture was heated at reflux temperature for 1 h. After cooling, the mixture was filtered and evaporated. The residue was suspended in ethyl acetate (200 ml) and water (100 ml). The phases were separated and the organic phase was washed with water (2×75 ml). The aqueous phases were extracted with ethyl acetate (100 ml) and the combined organic extracts were evaporated. The residue was suspended in warm cyclohexane (100 ml), and left cooling under stirring. The precipitated solid was filtered off and dried, affording 12H-dibenzo[d,g][1,3,6]dioxazocine (4.57 g, 50%).

The above dioxazocine (4.0 g, 19 mmol) was dissolved in dry N,N-dimethylformamide (150 ml). Sodium hydride (1.13 g, 28 mmol, 60% dispersion in oil) was added in portions, and the resulting mixture was stirred for 30 minutes at room temperature. 1-Bromo-3-chloropropane (4.6 ml, 47 mmol) was slowly added dropwise, and the reaction mixture was stirred at room temperature overnight. More sodium hydride (0.56 g, 14 mmol) was added, and stirring was continued for 6 h. More sodium hydride (0.56 g, 14 mmol) was added, and stirring was continued overnight. Ammonium chloride (3.2 g) was added, and the mixture was stirred for 30 minutes. Water was added (300 ml), and the mixture was extracted with dichloromethane (2×250 ml). The combined organic extracts were dried (MgSO$_4$) and evaporated. The residue was purified by column chromatography on silica gel using a mixture of heptane and ethyl acetate (6:1) as eluent. This afforded 12-(3-chloropropyl)-12H-dibenzo[d,g][1,3,6]dioxazocine (2.18 g, 40%).

The above chloride (1.35 g, 4.66 mmol) and potassium iodide (5.0 g, 30 mmol) in methyl ethyl ketone (150 ml) was heated at reflux temperature for 4.5 h. 2-(1-Piperazinyl)-3-pyridinecarboxylic acid ethyl ester (3.0 g, 12 mmol) was added followed by potassium carbonate (2.25 g, 16.3 mmol). The reaction mixture was heated at reflux temperature for 19 h. After cooling, the mixture was filtered, the filtercake was washed with methyl ethyl ketone, and the filtrate was evaporated. The residual oil was purified by column chromatography on silica gel (800 ml) using a mixture of heptane and ethyl acetate (1:3) as eluent. This afforded 2-(4-(3-(12H-dibenzo[d,g][1,3,6]dioxazocin-12-yl)-1-propyl)piperazin-1-yl)-3-pyridinecarboxylic acid ethyl ester (0.71 g, 32%) as an oil.

The above ester (0.50 g, 1.22 mmol), dissolved in a solution of sodium hydroxide (0.24 g, 6 mmol) in ethanol (30 ml) and water (3 ml) was stirred at room temperature for 25 h. The pH of the mixture was adjusted to 3 by addition of 1 N hydrochloric acid (6 ml). The mixture was extracted with dichloromethane (2×40 ml), the combined organic phases were washed with brine (50 ml), dried (MgSO$_4$) and the solvent was removed in vacuo. The residue was triturated with isopropyl acetate (15 ml) and the solid product was filtered off. Part of the product (275 mg) was suspended in acetone (160 ml), evaporated in vacuo and dried, affording the title compound (0.23 g, 75%).

Calculated for $C_{26}H_{28}N_4O_4$, 2 HCl; 0.5 $H_2O$, 0.5 $C_5H_{10}O_2$ C, 57.67%; H, 6.07%; N, 9.44%; Found: C, 57.78%; H, 6.02%; N, 9.42%.

HPLC retention time=18.42 minutes (5 μm C18 4×250 mm column, eluting with a 20–80% gradient of 0.1% trifluoriacetic acid/acetonitrile and 0.1% trifluoroacetic acid/water over 30 minutes at 30° C.

Example 4

2-(4-(3-(2-Chloro-12H-dibenzo[d,g][1,3,6]dioxazocin-12-yl)-1-propyl)-piperazin-1-yl)-3-pyridinecarboxylic acid dihydrochloride

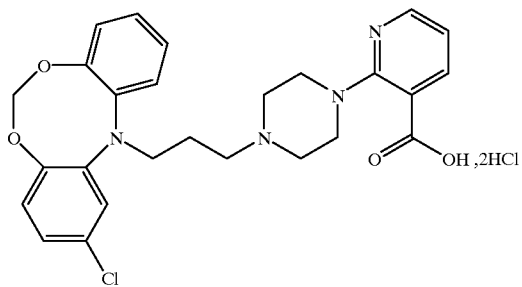

A suspension of 2-chloro-12H-dibenzo[d,g][1,3,6]dioxazocine (10.65 g, 43 mmol, described in J.Mol.Struct., 131, 1985, 131–140) and 3-chloropropionyl chloride (6.55 g, 51.6 mmol) in dry toluene (100 ml) was heated at reflux temperature for 5 h. After cooling to room temperature, the reaction mixture was washed with a saturated solution of sodium bicarbonate (50 ml). The organic layer was dried (MgSO$_4$), and evaporated in vacuo, affording 2-chloro-12-(3-chloropropionyl)-12H-dibenzo[d,g][1,3,6]dioxazocine (12.85 g, 88%).

To a cooled suspension of lithium aluminium hydride (3.0 g, 79 mmol) in dry tetrahydrofuran (80 ml), concentrated sulfuric acid (3.87 g, 39.5 mmol) was added dropwise at a rate to maintain a temperature <12° C. The mixture was stirred at room temperature for 1.5 h. A solution of the above amide (12.8 g, 37.8 mmol) in dry tetrahydrofuran (80 ml) was added dropwise and stirring was continued for 2 h. The reaction was quenched by careful addition of ethyl acetate (100 ml) followed by water (5.7 ml). Filtration of the mixture and evaporation of the filtrate in vacuo afforded 2-chloro-12-(3-chloropropyl)-12H-dibenzo[d,g][1,3,6]dioxazocine as a foam.

A mixture of the above crude chloride (1.14 g, 3.5 mmol), 2-(1-piperazinyl)-3-pyridinecarboxylic acid methyl ester (0.78 g, 3.5 mmol), dry potassium carbonate (1.45 g, 10.5 mmol), sodium iodide (0.53 g, 3.5 mmol) and 2-butanone (15 ml) was heated at reflux temperature for 48 h. The reaction mixture was evaporated in vacuo. The remainder was dissolved in toluene (25 ml), washed with water (2×25 ml) and evaporated in vacuo. The crude product (1.15 g) was purified by column chromatography on silica gel using a mixture of ethyl acetate and toluene (1:1) containing triethylamine (2.5%) as eluent. This afforded 2-(4-(3-(2-chloro-12H-dibenzo[d,g][1,3,6]dioxazocin-12-yl)-1-propyl)-1-piperazinyl)-3-pyridinecarboxylic acid methyl ester (1.10 g, 62%) as an oil.

The above ester (1.10 g, 2.16 mmol) was dissolved in ethanol (10 ml) and 2 N sodium hydroxide (3.57 ml, 7.13 mmol) was added. The mixture was stirred at room temperature for 16 h. The ethanol was evaporated in vacuo and the remainder was diluted with water (25 ml). pH was adjusted to 6 by addition of 6 N hydrochloric acid and the aqueous solution was extracted with dichloromethane (3×15 ml). The combined organic extracts were dried (MgSO$_4$) and evaporated in vacuo. The remainder was dissolved in tetrahydrofuran (25 ml) and a 2.5 N solution of hydrogen chloride in ether (1.67 ml, 4.18 mmol) was added dropwise. The mixture was stirred for 3 h, and the precipitate filtered off and dried to afford 0.86 g (75%) of the title compound.

M.p. 165–173° C.

Calculated for $C_{26}H_{27}ClN_4O_4$, 2 HCl: C, 54.99%; H, 5.15%; N, 9.87%; Found: C, 54.8%; H. 5.2%; N, 9.65%.

Example 5

1-(3-(10,11-Dihydro-5H-dibenzo[a,d]cyclohepten-5-ylidene)-1-propyl)-4-(2-pyridyl)piperazine dihydrochloride

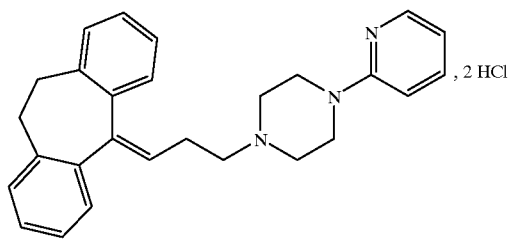

A mixture of 5-(3-bromo-1-propylidene)-10,11-dihydro-5H-dibenzo[a,d]cycloheptene (3.13 g, 10 mmol, prepared as described in WO 9518793), 1-(2-pyridyl)piperazine (2.5 g, 15 mmol, prepared similarly as described in J.Org,Chem. 1953, 18, 1484), potassium carbonate (2.8 g, 20 mmol) and N,N-dimethylformamide (40 ml) was stirred at room temperature for 16 h, and at 50–55° C. for 8 h. After cooling, the mixture was diluted with benzene (150 ml) and washed with water (3×100 ml). The organic layer was extracted with 3 N hydrochloric acid (100 ml). The acidic aqueous layer was made alkaline with 5 N sodium hydroxide (60 ml) to pH 12 and extracted with benzene (100 ml). The benzene solution was dried (K$_2$CO$_3$) and filtered over silica gel (12 g). Evaporation in vacuo provided an oil (2.98 g, 75%). This was dissolved in ethanol (20 ml), acidified with hydrogen chloride in diethyl ether (3 mmol/ml, 8 ml) and precipitated with diethyl ether (20 ml). The precipitate was filtered off, washed with diethyl ether and dried to give 2.1 g (44%) of the title compound.

M.p. 152–155° C.

Calculated for $C_{27}H_{29}N_3$, 2 HCl, H$_2$O: C, 66.66%; H, 6.84%;N, 8.64%; Cl, 14.58%; Found: C, 67.27%; H, 6.52%;N, 8.76%; Cl 14.19%.

Example 6

2-(4-(3-(10,11-Dihydro-5H-dibenzo[a,d]cyclohepten-5-ylidene)-1-propyl)-1-piperazinyl)-3-pyridine-carboxylic acid hydrochloride

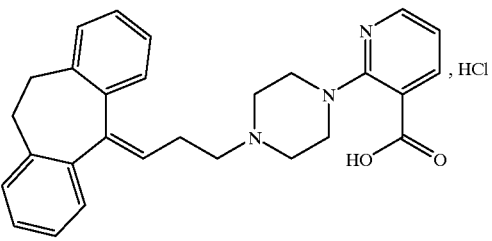

A mixture of 2-(1-piperazinyl)-3-pyridinecarboxylic acid ethyl ester (4.6 g, 0.019 mol), 3-(10,11-dihydro-5H-dibenzo[a,d]cyclohepten-5-ylidene)-1-propyl methanesulfonate (5.0 g, 0.015 mol) and potassium carbonate (4.8 g) in N,N-dimethylformamide (50 ml) was heated to 60° C. for 5 h. After standing overnight, the solid was filtered off and washed with benzene. The filtrate was diluted with benzene (200 ml) and washed with water (4×100 ml). The organic solution was dried (MgSO$_4$) and the solvent evaporated in vacuo. The residue (7.8 g) was purified by column chromatography on silica gel using benzene and a benzene-ethyl acetate mixture as eluents, affording 2-(4-(3-(10,11-dihydro-5H-dibenzo[a,d]cyclohepten-5-ylidene)-1-propyl)-1-piperazinyl)-3-pyridinecarboxylic acid ethyl ester (3.4 g, 48%) as an oil.

A mixture of the above ester (2.1 g, 4.5 mmol) and 20% sodium hydroxide (3.0 ml) in ethanol (21 ml) was stirred at room temperature for 16 h. The solution was poured into dichloromethane (250 ml) and acidified with 2 N hydrochloric acid. The organic phase was washed with water (10 ml), dried (MgSO$_4$) and the solvent evaporated in vacuo. The foamy residue was stripped with acetone and crystallized from acetone, affording 1.5 g (70%) of the title compound.

M.p. 224–230° C.

Calculated for $C_{28}H_{29}N_3O_2$, HCl, 0.25 H$_2$O, 0.5 C$_3$H6O: C, 69.53%; H, 6.63%; Cl, 6.96%; N, 8.25%; Found: C, 69.76%; H, 6.76%; Cl, 7.00%; N, 8.17%.

Example 7

2-(4-(2-(10,11-Dihydro-5H-dibenz[b,f]azepin-5-yl)-1-ethyl)-1-piperazinyl)-3-pyridinecarboxylic acid hydrochloride

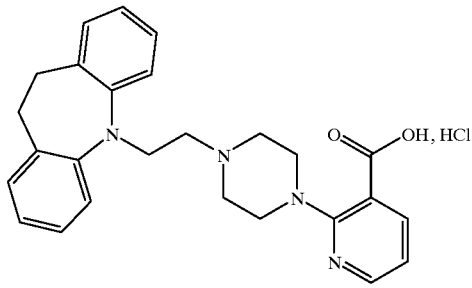

5-(2-Hydroxyethyl)-10,11-dihydro-5H-dibenz[b,f]azepine (2.5 g, 0.0104 mol, prepared similarly as described in Fr. Pat. 1,215 599) and triethylamine (2.8 g, 0.028 mol) was dissolved in benzene (90 ml). A solution of methanesulfonyl chloride (1.66 g, 0.0145 mol) in benzene (10 ml) was added dropwise at 15–20° C. for 10 minutes under cooling on a cold water bath. When addition was complete the reaction mixture was stirred 1 h at room temperature. Water (35 ml) was added, the organic layer was separated, washed with water (25 ml), dried ($MgSO_4$), and evaporated in vacuo. The methanesulfonate (3.2 g, 97%) was dissolved in acetone (55 ml) and 2-(1-piperazinyl)-3-pyridinecarboxylic acid ethyl ester (2.64 g, 0.0112 mol) and potassium carbonate (4.0 g) were added. The reaction mixture was heated at 50–55° C. for 28 h. The mixture was filtered and the solvent was removed by evaporation in vacuo. The crude residue (5.7 g) was purified by column chromatography on silica gel (65 g) using a mixture of benzene and chloroform as eluent. This afforded 2.0 g (43%) of 2-(4-(2-(10,11-dihydro-5H-dibenz[b,f]azepin-5-yl)-1-ethyl)-1-piperazinyl)-3-pyridinecarboxylic acid ethyl ester as an oil.

The above ester was dissolved in ethanol (5 ml) and 4 N sodium hydroxide (5 ml) was added. The mixture was stirred at room temperature for 16 h. Dichloromethane (200 ml) was added followed by concentrated hydrochloric acid (3 ml). The solid was filtered off, washed with acetone, stirred with water (2×25 ml), filtered and washed with acetone. The crude product was dissolved in warm N,N-dimethylformamide, benzene was added and the mixture was cooled overnight. The precipitate was filtered off, washed with benzene and dried, affording 0.9 g (44%) of the title compound.

M.p. 240–245° C.

Calculated for $C_{26}H_{28}N_4O_2$, HCl, 0.5 $H_2O$: C, 65.87%; H, 6.38%; N, 11.82%; Cl, 7.48%; Found: C, 65.82%; H, 6.23%; N, 11.66%; Cl, 7.90%.

Example 8

6-(4-(3-(10,11-Dihydro-5H-dibenz[b,f]azepin-5-yl)-1-propyl)-1-piperazinyl)-2-pyridinecarboxylic acid hydrochloride

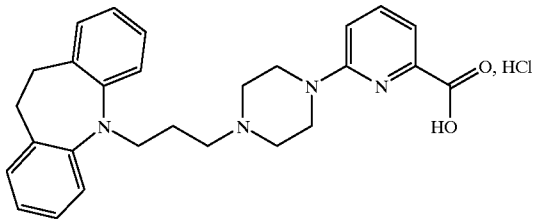

To a suspension of 6-chloropyridine-2-carboxylic acid (8.3 g, 0.0525 mol, prepared as described in Chem.Ber.45, 2456 (1912)) in dioxane (25 ml), thionyl chloride (9.4 ml, 0.13 mol) was added and the resulting mixture was stirred at 70° C. for 4 h. The reaction mixture was concentrated in vacuo and a mixture of dioxane (8.3 ml) and ethanol (16.6 ml) was added. The reaction mixture was heated to 70° C. for 2 h, triethylamine (8.3 ml), ethanol (4.1 ml) and water (8.3 ml) were added and the reaction mixture was again concentrated. The residue was distributed between diethyl ether (28 ml) and water (18 ml) and the phases were separated. The aqueous layer was extracted with diethyl ether (30 ml) and the combined organic layers were dried ($MgSO_4$) and evaporated in vacuo. This afforded 8.82 g (91%) of 6-chloropyridine-2-carboxylic acid ethyl ester as an oil.

A mixture of the above ester (8.6 g, 0.046 mol), anhydrous piperazine (41 g, 0.476 mol) and sodium iodide (0.46 g) in toluene (145 ml) were heated at reflux temperature for 2.5 h. After cooling to about 80° C., piperazine was filtered off and the filtrate was mixed with water (250 ml) and diethyl ether (100 ml). The organic layer was separated and washed with water (2×50 ml) and brine (50 ml), dried ($MgSO_4$) and evaporated, affording 4.6 g of an oil. The aqueous layer was extracted with chloroform (5×50 ml), the combined organic phases were washed with water and brine as above, dried and evaporated, affording an additional 3.2 g of an oil. Both crops were purified by column chromatography on silica gel (200 g) using a mixture of chloroform and ethanol (9:1) as eluent. This afforded 5 g (46%) of 6-(1-piperazinyl)-2-pyridinecarboxylic acid ethyl ester as an oil.

A mixture of the above ester (2.20 g, 9.35 mmol), (10,11-dihydro-5H-dibenzo[b,f]-azepin-5-yl)-1-propyl)methane sulfonate (2.82 g, 8.51 mmol) and potassium carbonate (3.3 g, 0.0239 mol) in acetone (47 ml) was heated at reflux temperature for 16 h. The reaction mixture was filtered and concentrated in vacuo. The residue was purified by column chromatography on silica gel (100 g) using chloroform as eluent. This afforded 1.21 g (30%) of 6-(4-(3-(10,11-dihydro-5H-dibenzo[b,f]-azepin-5-yl)-1-propyl)-1-piperazinyl)-2-pyridinecarboxylic acid ethyl ester as an oil.

A mixture of the above ester (1.06 g, 2.25 mmol), ethanol (10 ml), a solution of sodium hydroxide (0.342 g) and water (1.3 ml) was stirred at room temperature for 48 h. Concentrated hydrochloric acid (1.25 ml) was added followed by dichloromethane (60 ml). The phases were separated, and the organic phase was dried ($MgSO_4$) and evaporated in vacuo. The residue was re-evaporated with acetone (30 ml) and stirred with hot ethanol (30 ml). This afforded after drying, 0.45 g (42%) of the title compound.

Calculated for C$_{27}$H$_{30}$N$_4$O$_2$, HCl: C, 67.70%; H, 6.52%; N, 11.70%; Cl, 7.40%; Found: C, 67.26%; H, 6.70%; N, 11.63%; Cl, 7.31%.

Example 9

2-(4-(3-(10,11-Dihydro-5H-dibenz[b,f]azepin-5-yl)-1-propyl)-1-piperazinyl)-3-pyridinecarboxylic acid dihydrochloride

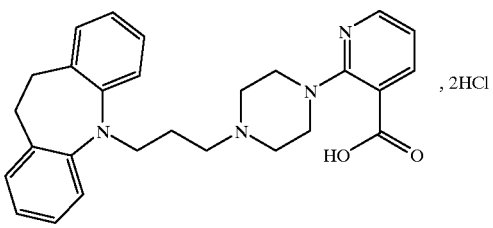

A mixture of 5-(3-chloropropyl)-10,11-dihydro-5H-dibenz[b,f]azepine (4.54 g, 16.7 mmol), 2-piperazinyinicotinic acid methyl ester 3.7 g, 16.7 mmol), dry potassium carbonate (6.92 g, 50.1 mmol), sodium iodide (2.5 g, 16.7 mmol) and 2-butanone (50 ml) was heated at reflux temperature for 60 h. After cooling to room temperature, toluene (100 ml) and water (100 ml) were added. The organic layer was separated, washed with water (2×50 ml) and evaporated in vacuo. The crude product was purified by column chromatography on silica gel using a mixture of toluene and ethyl acetate (3:1) containing triethylamine (2.5%) as eluent. This afforded 2.3 g (30%) of 2-(4-(3-(10,11-dihydro-5H-dibenz[b,f]azepin-5-yl)-1-propyl)-1-piperazinyl)-3-pyridinecarboxylic acid methyl ester as an oil.

A mixture of the above ester (2.3 g, 5.04 mmol) dissolved in a mixture of 2 N sodium hydroxide (8.32 ml, 16.63 mmol) and ethanol (25 ml) was stirred at room temperature for 16 h. The ethanol was evaporated in vacuo and the remainder was diluted with water (50 ml). 2 N Hydrochloric acid (20 ml) was added, and the solution was washed with diethyl ether (25 ml). The aqueous phase was extracted with dichloromethane (3×30 ml). The combined organic extracts were dried (MgSO$_4$) and evaporated in vacuo to afford a foam. This was crystallized from tetrahydrofuran, filtered and dried, affording 1.20 g (50%) of the title compound.

M.p. 168–171° C.

Calculated for C$_{27}$H$_{30}$N$_4$O$_2$, 1.75 HCl: C,64.04%; H,6.32%; N,11.06%; Cl,12.25%; Found: C,63.72%; H,6.42%; N,10.68%; Cl,11.99%.

Example 10

2-(4-(3-(10,11-Dihydro-5H-dibenzo[b,f]azepin-5-yl)-1-propyl)-1-piperazinyl)-5-pyridinecarboxylic acid hydrochloride

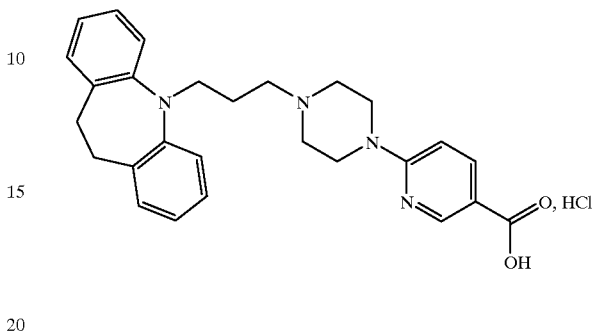

A mixture of 2-bromopyridine-5-carboxylic acid methyl ester (1.40 g, 6.5 mmol) and piperazine (5.59 g, 65 mmol) was dissolved in acetonitrile (50 ml) and heated at reflux temperature for 2.5 h. The reaction mixture was concentrated in vacuo, dissolved in dichloromethane (50 ml) and extracted with water (3×50 ml). The organic solution was dried (MgSO$_4$) and evaporated in vacuo, affording 0.80 g (56%) of 2-(1-piperazinyl)-5-pyridinecarboxylic acid methyl ester.

M.p. 91–92° C.

A mixture of the above ester (0.73 g, 3.3 mmol), 5-(3-chloropropyl)-10,11-dihydro-5H-dibenzo[b,f]azepine (0.9 g, 3.3 mmol), dry potassium carbonate (1.37 g, 9.9 mmol), sodium iodide (0.5 g, 3.3 mmol) and 2-butanone (10 ml) was heated at reflux temperature for 24 h. After cooling to room temperature, dichloromethane (25 ml) and water (25 ml) were added to the reaction mixture. The organic layer was separated, washed with water (2×10 ml) and evaporated in vacuo. The crude residue was purified by column chromatography on silica gel using a mixture of toluene and ethyl acetate (1:1) containing triethylamine (2.5%) as eluent. This afforded 0.65 g (43%) of 2-(4-(3-(10,11-dihydro-5H-dibenz[b,f]azepin-5-yl)-1-propyl)-1-piperazinyl)-5-pyridinecarboxylic acid methyl ester as an oil.

The above ester (0.65 g, 1.25 mmol), dissolved in a mixture of 2 N sodium hydroxide (2.06 ml, 4.13 mmol) and ethanol (10 ml) was stirred at room temperature for 16 h. The ethanol was evaporated in vacuo and the remainder was diluted with water (30 ml). 2 N Hydrochloric acid (20 ml) was added and the solution was washed with diethyl ether (25 ml). The aqueous phase was extracted with dichloromethane (3×15 ml). The combined organic extracts were dried (MgSO$_4$) and concentrated in vacuo to 20 ml. The precipitate was filtered off and dried to afford 0.33 g (60%) of the title compound.

M.p. 240–244 ° C.

Calculated for C$_{27}$H$_{30}$N$_4$O$_2$, HCl, 0.5 H$_2$O: C,66.45%; H,6.61%; N,11.48%; Cl,7.26%; Found: C,66.39%; H,6.64%; N,11.22%; Cl,7.08%.

Example 11

2-(4-(3-(3-Chloro-10,11-dihydro-5H-dibenzo[b,f]azepin-5-yl)-1-propyl)-1-piperazinyl)-3-pyridinecarboxylic acid dihydrochloride

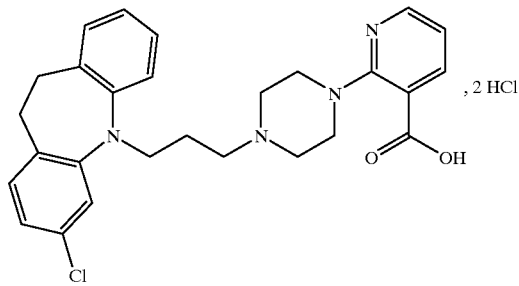

To a solution of 3-chloro-10,11-dihydro-5H-dibenzo[b,f]azepine (5.0 g, 22 mmol) in toluene (20 ml), 3-chloropropionyl chloride (3.32 g, 26 mmol) in toluene (8 ml) was added dropwise. The reaction mixture was stirred at 95° C. for 2 h and left stirring at room temperature overnight. 2 N Sodium hydroxide (25 ml) followed by toluene (50 ml) were added, and the phases were separated. The toluene phase was washed with 2 N sodium hydroxide (2×25 ml), water (3×30 ml) and brine (30 ml). The organic phase was dried (MgSO$_4$) and evaporated in vacuo. The residue was stripped with methanol (30 ml) and the residue was suspended in ethyl acetate (8 ml), stirred and filtered off. The solid was washed with ethyl acetate (10 ml) and dried. This afforded 4.0 g (57%) of 3-chloro-1-(3-chloro-10,11-dihydro-5H-dibenzo[b,f]azepin-5-yl)propan-1-one.

A 1.0 M solution of lithium aluminium hydride in tetrahydrofuran (26.2 ml, 26 mmol) was introduced into a 250 ml dry three-necked flask under nitrogen. Under cooling (ice bath), concentrated sulphuric acid (0.7 ml) was slowly added dropwise. The mixture was stirred for 15 minutes on an ice bath and subsequently 45 minutes at room temperature. The above amide (4.2 g, 13 mmol) was dissolved in tetrahydrofuran (40 ml) and slowly added dropwise. The reaction mixture was left stirring for 1.5 h. Water (1 ml) was added dropwise, followed by 4 N sodium hydroxide (1 ml) and subsequently water (3 ml). The mixture was left stirring for 30 minutes, filtered (hyflo) and evaporated. The residue was dissolved in ethyl acetate (50 ml), dried (MgSO$_4$) and evaporated to give 3.5 g (88%) of 3-chloro-5-(3-chloropropyl)-10,11-dihydro-5H-dibenzo[b,f]azepine.

Potassium iodide (2.8 g, 17 mmol) and methyl ethyl ketone (70 ml) was heated at 80° C. for 1 h. The above chloride (0.8 g, 3 mmol) was dissolved in methyl ethyl ketone (10 ml) and added. The mixture was heated at reflux temperature for 50 minutes. Potassium carbonate (1.25 g, 9 mmol) was added followed by 2-(1-piperazinyl)-3-pyridine carboxylic acid methyl ester (1.0 g, 4 mmol) in methyl ethyl ketone (10 ml). The reaction mixture was stirred at 78° C. overnight. After cooling, the mixture was filtered (hyflo) and evaporated. The residue was purified by column chromatography on silica gel using a mixture of heptane and ethyl acetate (1:1) as eluent. This afforded 0.33 g (26%) of 2-(4-(3-(3-chloro-10,11-dihydro-5H-dibenzo[b,f]azepin-5-yl)-1-propyl)-1-piperazinyl)-3-pyridine carboxylic acid ethyl ester.

TLC: R$_f$=0.17 (SiO$_2$: ethyl acetate/heptane=1:1).

The above ethyl ester (0.33 g, 0.67 mmol) was dissolved in ethanol (8 ml). 4 N Sodium hydroxide (0.34 ml) was added, and the reaction mixture was stirred for 2 h at room temperature, and left in a freezer overnight. Stirring at room temperature was continued for 24 h. More 4 N sodium hydroxide (0.34 ml) was added, stirring was continued for 2 h, additional 4 N sodium hydroxide was added (0.34 ml) and stirring was continued for 3.5 h. 4 N Hydrochloric acid (1.18 ml) was added, followed by water (20 ml) and dichloromethane (100 ml). The phases were separated, and the organic phase was dried (MgSO$_4$) and evaporated. The residue was stripped with acetone (2×30 ml), stirred with isopropyl acetate (3–5 ml) for 5 minutes, filtered off and dried. Yield 0.18 g (51%) of the title compound as an amorphous powder.

Calculated for C$_{27}$H$_{29}$ClN$_4$O$_2$, 2HCl, 0.25 C$_5$H$_9$O$_2$: C, 62.98%; H, 6.03%; N, 10.40%; Found: C, 63.31%; H, 6.36%; N, 10.16%.

HPLC retention time=23.82 minutes (5 μm C184×250 mm column, eluting with a 20–80% gradient of 0.1% trifluoriacetic acid/acetonitrile and 0.1% trifluoroacetic acid/water over 30 minutes at 30° C.

Example 12

1-(3-(10,11-Dihydro-5H-dibenzo[a,d]cyclohepten-5-ylidene)-1-propyl)-4-(2-nitrophenyl)-piperazine hydrochloride

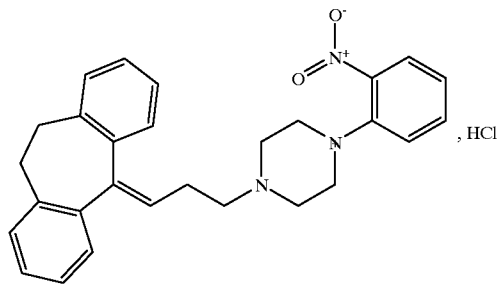

2-Fluoronitrobenzene (11.4 g, 81 mmol) was dissolved in dimethylsulfoxide (200 ml), and piperazine (56.4 g, 0.65 mol) and sodium carbonate (20.6 g, 0.2 mol) were added. The mixture was stirred at 130° C. for 16 h. After cooling, toluene (300 ml) was added and the mixture was washed with water (3×300 ml) and 1 N sodium hydroxide (300 ml). The organic phase was dried (MgSO$_4$) and concentrated in vacuo. The residue was purified by flash chromatography on silica gel, eluting first with a mixture of ethyl acetate, heptane and triethyl amine (5:5:0.25), then with a mixture of ethyl acetate and triethyl amine (9:1), and finally with a mixture of methanol and triethyl amine (40:1). This afforded 1-(2-nitrophenyl)-piperazine (8.08 g, 48%).

TLC: R$_f$=0.27 (SiO$_2$: ethyl acetate/methanol/triethyl amine=1:1:0.025)

The above piperazine (1.51 g, 7.3 mmol) was dissolved in methyl ethyl ketone (50 ml), and 5-(3-bromo-1-propylidene)-10,11-dihydro-5H-dibenzo[a,d]cycloheptene (2.28 g, 7.3 mmol), potassium iodide (0.96 g, 15 mmol) and potassium carbonate (6.0 g, 44 mmol) were added, and the resulting mixture was stirred at reflux temperature for 24 h. After cooling, ethyl acetate (100 ml) was added and the mixture was washed with water (2×100 ml), dried (MgSO$_4$) and concentrated in vacuo. The residue was purified by flash chromatography on silica gel using a mixture of ethyl acetate and heptane (1:2) as eluent, to give 2.18 g (68%) of the free base. This was dissolved in diethyl ether (30 ml) and 1N hydrochloric acid in diethyl ether (5 ml) was added. The precipitated solid was isolated by filtration and dried in vacuo to give 1.83 g (53%) of the title compound as a solid.

M.p. 204–206° C.

Calculated for $C_{28}H_{29}N_3O_2$, HCl: C, 70.65%; H, 6.35%; N, 8.83%; Found: C, 70.50%; H, 6.51%; N, 8.61%.

Example 13

2-(4-(3-(10,11-Dihydro-5H-dibenzo[a,d] cyclohepten-5-ylidene)-1-propyl)-1-piperazinyl) benzonitrile

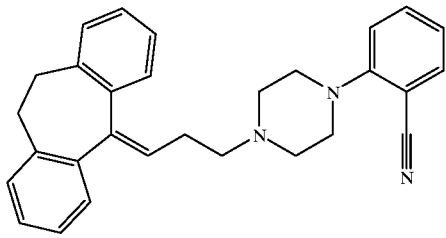

Piperazine (6.0 g, 69 mmol) was dissolved in dimethylsulfoxide (50 ml), 2-fluorobenzonitrile (0.95 ml, 9 mmol) and potassium carbonate (2.2 g, 17 mmol) were added and the mixture was stirred at room temperature for 16 h. Water (100 ml) was added and the mixture was extracted with toluene (2×100 ml). The combined organic extracts were washed with 1N sodium hydroxide (3×75 ml), dried ($MgSO_4$) and concentrated in vacuo to give 1.48 g (88%) 2-(1-piperazinyl)benzonitrile as an oil.

TLC: $R_f$=0.12 ($SiO_2$: ethyl acetate/triethyl amine=4:1).

The above benzonitrile (4.89 g, 26 mmol) was dissolved in methyl ethyl ketone (100 ml), and potassium carbonate (21.7 g, 157 mmol), potassium iodide (3.45 g, 52 mmol), and 5-(3-bromo-1-propylidene)-10,11-dihydro-5H-dibenzo[a,d] cycloheptene (8.18 g, 26 mmol), were added. The resulting mixture was stirred at reflux temperature for 18 h. After cooling to room temperature, ethyl acetate (200 ml) was added and the mixture was washed with water (2×150 ml), dried ($MgSO_4$) and concentrated in vacuo. The residue was purified by flash chromatography on silica gel eluting first with a mixture of ethyl acetate and heptane (1:4), and then with a mixture of ethyl acetate and heptane (1:2). This afforded 5.60 g of the title compound as a solid.

M.p. 112–114° C.

Calculated for $C_{29}H_{29}N_3$: C, 83.02%; H, 6.97%; N, 10.02%; Found: C, 83.25%; H, 7.14%; N, 9.93%.

Example 14

2-(4-(3-(10,11-Dihydro-5H-dibenzo[a,d] cyclohepten-5-ylidene)-1-propyl)-1-piperazinyl)-benzoic acid hydrochloride

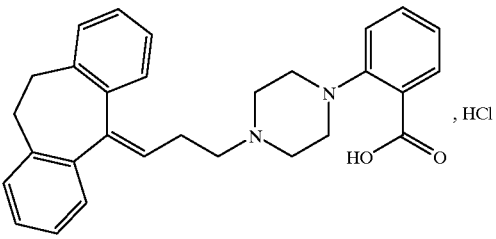

2-(4-(3-(10,11-Dihydro-5H-dibenzo[a,d]cyclohepten-5-ylidene)-1-propyl)-1-piperazin)-benzonitrile (0.30 g, 0.72 mmol, prepared as described in example 13) was added to a mixture of water (0.6 ml), sulphuric acid (0.6 ml), and acetic acid (0.6 ml). The resulting mixture was heated at reflux temperature for 24 h and stirred at room temperature for 3 days. 1 N Sodium hydroxide (20 ml) was added and the mixture was washed with diethyl ether (3×20 ml). The aqueous phase was acidified with 5 N hydrochloric acid to pH 1. The mixture was extracted with dichloromethane (2×50 ml), the combined extracts were dried ($MgSO_4$) and evaporated in vacuo to give 0.21 g (56%) of the title compound as an amorphous solid.

Calculated for $C_{29}H_{23}N_2O_2$, HCl, 1.5 $H_2O$: C, 69.38%; H, 6.83%; N, 5.58%; Found: C, 69.69%; H, 6.69%; N, 5.06%.

El-MS (70 eV): m/e=438 ($M^+$, 0.1%)

Example 15

1-(3-(10,11-Dihydro-5H-dibenzo[a,d]cyclohepten-5-ylidene)-1-propyl)-4-(3-trifluoromethyl-2-pyridyl) piperazine, dihydrochloride

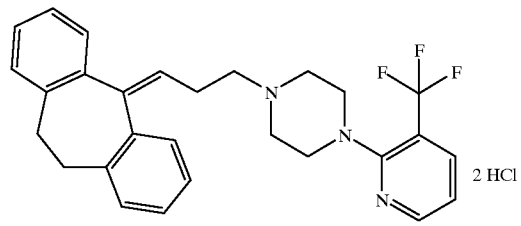

A mixture of 5-(3-bromo-1-propylidene)-10,11-dihydro-5H-dibenzo[(a,d)]cycloheptene (1.10 g, 3.5 mmol, prepared similarly as described in WO 9518793), 1-(3-(trifluoromethyl)-2-pyridyl)piperazine (0.81 g, 3.5 mmol), potassium carbonate (1.45 g, 10.5 mmol) and sodium iodide (0.53 g, 3.5 mmol) in dry 2-butanone (10 ml) was heated at reflux temperature for 40 h. The solvent was removed in vacuo and the remainder was dissolved in toluene (25 ml) and water (25 ml). The organic layer was separated, dried ($MgSO_4$) and concentrated in vacuo. The residue was purified by flash chromatography on silica gel using a mixture of toluene and ethyl acetate (3:1) containing 2.5% triethylamine as eluent, to give 1.54 g (95%) of the free base. This was dissolved in tetrahydrofuran (25 ml) and 1 N hydrogen chloride in diethyl ether (7 ml) was added. The precipitated solid was isolated by filtration and dried in vacuo to give 1.45 g (77%) of the title compound as a solid.

M.p. 225–227° C.

Calculated for $C_{28}H_{28}N_3F_3$, 2HCl: C, 62.69%; H, 5.64%; N, 7.83%; Found: C, 61.99%; H, 5.82%; N, 7.60%.

Example 16

2-(4-(2-(6,11-Dihydro-dibenzo[b,e]thiepin-11-ylidene)ethyl)piperazin-1-yl)-3-pyridinecarboxylic acid, dihydrochloride

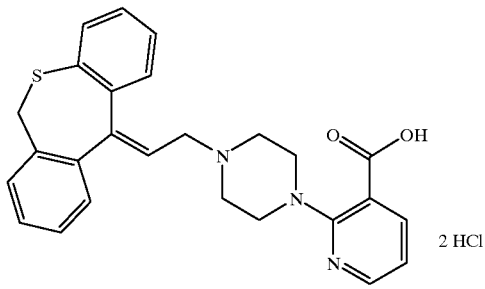

A mixture of 11-(2-bromoethylidene)-6,11-dihydrodibenzo[b,e]thiepine (2.5 g, 7.9 mmol, prepared similarly as described in Coll. Czech. Chem. Comm. 52, 1566 (1987)), ethyl 2-(1-piperazinyl)-3-pyridinecarboxylate (1.86 g, 7.9 mmol), potassium carbonate (1.45 g, 10.5 mmol) and N,N-dimethylformamide (15 ml) was stirred and heated at 150° C. for 10 h. The mixture was diluted with water and extracted with benzene (50 ml). The organic phase was dried (potassium carbonate), filtered and the solvent was evaporated in vacuo. The oily residue was purified on silica gel (50 g), using ethyl acetate as eluent to give the base which was dissolved in diethyl ether and neutralised with oxalic acid in acetone. This afforded 2.7 g (54%) of ethyl 2-(4-(2-(6,11-dihydrodibenzo[b,e]thiepin-11-ylidene)ethyl)-1-piperazinyl)-3-pyridinecarboxylate hydrogen oxalate hemihydrate.

TLC: $R_f$=0.5 ($SiO_2$: chloroform/ethanol/ammonia=40:2:1).

The above ester (2.25 g, 4.77 mmol) was dissolved in ethanol (40 ml) and 5 N sodium hydroxide (3 ml) was added. The mixture was stirred at 40° C. for 20 h, ethanol was evaporated in vacuo and water (40 ml) followed by acetic acid (2 ml) were added. The mixture was extracted with dichloromethane (50 ml), the organic phase was dried (MgSO₄) and the solvent was evaporated in vacuo. The residue was dissolved in acetone and neutralised with hydrogen chloride in diethyl ether, affording 2.13 g (85%) of the title compound as hemihydrate.

M.p. 188–195° C.

Calculated for $C_{26}H_{25}N_3O_2S$, 0.5 $H_2O$, 2 HCl: C, 59.42%; H, 5.37%; N, 8.00%; Cl, 13.49%; S, 6.10%; Found: C, 58.94%; H, 5.23%; N, 8.10%; Cl, 13.44%; S, 5.80%.

Example 17

2-(4-(3-(6,11-Dihydrodibenzo[b,e]thiepin-11-ylidene)-1-propyl)-1-piperazinyl)-3-pyridinecarboxylic acid dihydrochloride

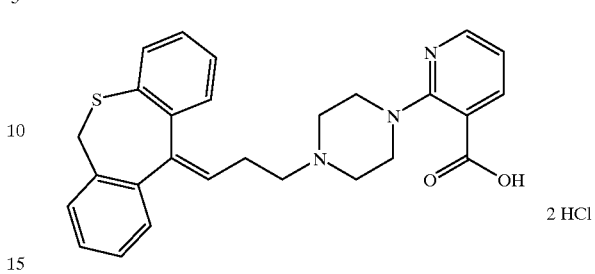

A solution of cyclopropylmagnesium bromide in dry tetrahydrofuran (prepared from cyclopropyl bromide (3.7 g, 0.031 mol), magnesium turnings (0.8 g, 0.033 mol) and dry tetrahydrofuran (50 ml) under an atmosphere of nitrogen) was added dropwise to a solution of (6,11-dihydrodibenzo[b,e]thiepin-11-one (3.5 g, 0.016 mol, similarly prepared as described in Chem. Pharm. Bull. 39, 1991, 2564) in dry tetrahydrofuran (50 ml). When addition was complete, the mixture was heated at 50° C. for 2 h. The reaction mixture was cooled on an ice-bath and saturated ammonium chloride (50 ml) and water (50 ml) were carefully added. The mixture was extracted with diethyl ether (2×100 ml), dried (MgSO₄), filtered and the solvent was evaporated in vacuo to give 4.4 g of crude 11-cyclopropyl-6,11-dihydro-11H-dibenzo[b,e]thiepin-11-ol as an oil.

The above crude alcohol (4.0 g) was dissolved in dichloromethane (50 ml) and a solution of trimethylsilyl bromide (2.1 ml, 0.016 mol) was added dropwise at room temperature. When addition was complete the mixture was stirred at room temperature for 1.5 h and water (50 ml) was added. The phases were separated and the organic phase was washed with water (50 ml), dried (MgSO₄) and the solvent was evaporated in vacuo to give 4.1 g (83%) of crude 1-bromo-3-(6,11-dihydro-dibenzo[b,e]thiepin-11-ylidene)propane as a solid.

TLC: $R_f$=0.55 ($SiO_2$: benzene/cyclohexane=1:3).

A mixture of the above bromide (3.65 g, 0.011 mol), 2-piperazinyl-3-pyridinecarboxylic acid ethyl ester (3.11 g, 0.0132 mol), potassium carbonate (4.55 g, 0.033 mol) and sodium iodide (1.61 g, 0.011 mol) in 2-butanone (53 ml) was heated at reflux temperature for 6 h. After standing overnight, the reaction mixture was filtered and the filtrate evaporated in vacuo. The oily residue was purified by column chromatography on silica gel (70 g) using chloroform as eluent. This afforded 4.87 g (91%) of 2-(4-(3-(6,11-dihydrodibenzo[b,e]thiepin-11-ylidene)-1-propyl)-1-piperazinyl)-3-pyridinecarboxylic acid ethyl ester as an oil.

TLC: $R_f$=0.42 ($SiO_2$: ethyl acetate/n-hexane=1:1).

The above ester (2.77 g, 0.0057 mol) was dissolved in ethanol (46 ml) and 4 N sodium hydroxide (6.34 ml, 0.024 mol) was added. The mixture was left at room temperature overnight. Concentrated hydrochloric acid (4.76 ml) and dichloromethane (300 ml) were added and the organic layer was separated, dried (MgSO₄) and evaporated in vacuo. The residue was stripped with dichloromethane (3×80 ml). After stirring with a mixture of acetone (100 ml) and diethyl ether (100 ml), 0.75 g (24%) of the title compound was obtained.

M.p. 161–166° C.

Calculated for $C_{27}H_{27}N_3O_2S$, 2 HCl, $H_2O$: C, 59.12%; H, 5.70%; N, 7.66%; S, 5.85%; Found: C, 59.27%; H, 5.61%; N, 7.54%; S, 6.13%.

Example 18

2-(4-(2-(6,11-Dihydrodibenzo[b,e]thiepin-11-yloxy)ethyl)-1-piperazinyl)-3-pyridinecarboxylic acid

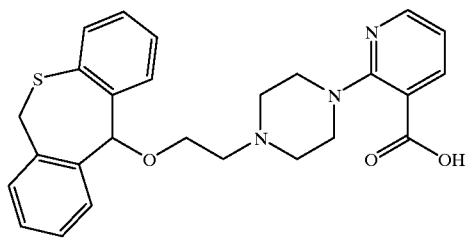

6,11-Dihydrodibenzo(b,e)thiepin-11-ol (13.2 g, 0.0578 mol, prepared similarly as described in Ceskoslov. Farm. 11, 404 (1962)) was dissolved in benzene (160 ml) and 2-bromoethanol (10.8 g, 0.086 mol) and concentrated sulphuric acid (2 ml) were added. The mixture was stirred at ambient temperature for 2 h and after standing overnight ice-water was added and the phases were separated. The organic phase was washed with 5% sodium bicarbonate, dried (MgSO$_4$) and the solvent was evaporated in vacuo affording a residue which was crystallized from a mixture of benzene and cyclohexane. This afforded 13.5 g (70%) of 11-(2-bromethoxy)-6,11-dihydrodibenzo[b,e]thiepine as a solid.

TLC: R$_f$=0.08 (SiO$_2$: cyclohexane/ethyl acetate=5:1).

A mixture of the above bromide (2.85 g, 8.5 mmol), ethyl 2-(1-piperazinyl)-3-pyridinecarboxylate (2.0 g, 8.5 mmol), potassium carbonate (1.65 g, 12 mmol) and N,N-dimethylformamide (15 ml) was stirred and heated at 150° C. for 10 h. The mixture was diluted with water and extracted with benzene (50 ml). The organic phase was dried (potassium carbonate), filtered and the solvent was evaporated in vacuo. The oily residue was purified on silica gel (50 g), using ethyl acetate as eluent to give the free base which was dissolved in diethyl ether and neutralised with oxalic acid in acetone, affording 3.75 g (74%) of ethyl 2-(4-(6,11-dihydrodibenzo[b,e]thiepin-11-yloxyethyl)-1-piperazinyl)-3-pyridinecarboxylate hydrogen oxalate hydrate was obtained as crystals. The free base was released from the above oxalate with aqueous ammonia and isolated by extraction with diethyl ether.

TLC: R$_f$=0.55 (SiO$_2$: chloroform/ethanol/ammonia=40:2:1).

The above free ester (2.65 g, 5.4 mmol) was dissolved in ethanol (40 ml) and 5 N sodium hydroxide (4 ml) was added. The mixture was stirred at 40° C. for 20 h, ethanol was evaporated in vacuo, and water (40 ml) followed by acetic acid (3 ml) were added. The mixture was extracted with dichloromethane (50 ml). The product crystallizing from this solution was filtered off. Dichloromethane was evaporated from the mother liquor and the second crop of the product was obtained by trituration with acetone, yielding a total amount of 2.4 g (95%) of the title compound.

M.p. 217–218.5° C.

Calculated for C$_{26}$H$_{27}$N$_3$O$_3$S, 0.25 H$_2$O : C, 67.00%; H, 5.95%; N, 9.02%; S, 6.88%; Found: C, 67.18%; H, 5.84%; N, 8.99%; S, 6.64%.

Example 19

6-(4-(3-(10,11-Dihydro-5H-dibenzo[a,d]cyclohepten-5-ylidene)-1-propyl)piperazin-1-yl)-2-pyridinecarboxylic acid hydrochloride

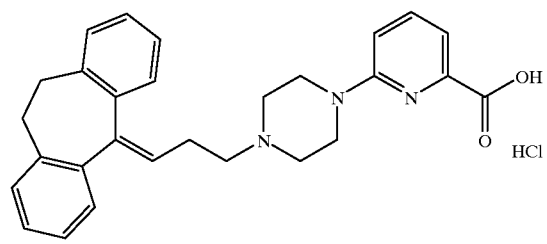

To a solution of 6-piperazinyl-2-pyridine carboxylic acid ethyl ester (7.0 g, 0.03 mol) in 2-butanone (150 ml), 3-(10,11-dihydro-5H-dibenzo[a,d]-cyclohepten-5-yliden1)-1-propyl methanesulfonate (6.8 g, 0.0207 mol) and potassium carbonate (8.0 g) were added. The reaction mixture was heated at 40° C. for 3 h. After standing overnight at room temperature, heating was continued at 60° C. for 9 h and at reflux temperature for 9 h. The solid was filtered off, washed with acetone and the filtrate was evaporated in vacuo. The residue was purified by column chromatography on silica gel (200 g) using chloroform as eluent. This afforded 6.63 g (68%) of 6-(4-(3-(10,11-dihydro-5H-dibenzo[a,d]cyclohepten-5-ylidene)-1-propyl)piperazin-1-yl)-2-pyridinecarboxylic acid ethyl ester as an oil.

TLC: R$_f$=0.32 (SiO$_2$: petroleum ether/ethyl acetate=3:2).

To a solution of the above ester (3.74 g, 8.0 mmol) in ethanol (38 ml), a solution of sodium hydroxide (1.3 g) in water (4.9 ml) was added and the reaction mixture was left at room temperature for 60 h. Concentrated hydrochloric acid (4.9 ml) was added followed by dichloromethane (230 ml). The mixture was stirred for 5 minutes, the phases were separated and the organic phase dried (MgSO$_4$) and evaporated in vacuo. The foamy residue was dissolved in acetone (500 ml) and evaporated to one third of its volume. The formed solid was filtered off, yielding 1.8 g (47%) of the title compound.

M.p.233–243° C.

Calculated for C$_{28}$H$_{29}$N$_3$O$_2$, HCl, 0.25 H$_2$O: C, 69.98%, H, 6.40%, Cl, 8.74%, N, 7.38%, Found: C, 69.90%, H, 6.42%, Cl, 8.47%, N, 7.52%.

Example 20

2-(4-(3-(3-Methyl-10,11-dihydro-5H-dibenzo[b,f]azepin-5-yl)-1-propyl)-1-piperazinyl)-3-pyridinecarboxylic acid hydrochloride

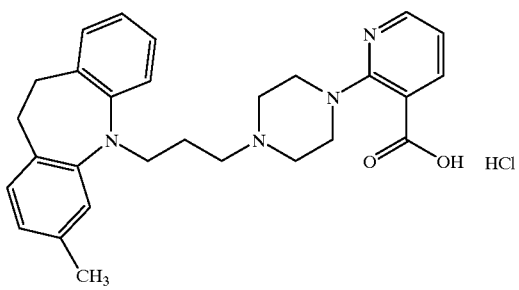

Under nitrogen and with magnetic stirring on an oil bath, sodium (3.14 g, 0.136 mol) was heated at 120–130° C. until melted and then methanol (6.1 ml, 0.15 mol) was added dropwise. As some unreacted sodium remained, additional methanol (1 ml) was added. At the same temperature, the alcoholate was heated for 1 h and the white loose solid was cooled on ice-salt bath and at 10–15° C. A mixture of diethyl 2-bromophenylmethylphosphonate (27.94 g, 0.091 mol) and 4-methyl-2-nitrobenzaldehyde (15.02 g, 0.091 mol, prepared similarly as described in Zh.Org.Khim.1968, 5, 953 or in Ann.1956, 627, 218) in N,N-dimethylformamide (60 ml) was added dropwise. When the addition was complete, the reaction mixture was stirred for additional 20 minutes at the same temperature, maintained at room temperature under light cooling on a water bath for additional 1 h and left to stand overnight in the refrigerator. Water (150 ml) was added under cooling on an ice bath, the reaction mixture was diluted with additional water (450 ml) and extracted with ethyl acetate (5×100 ml). The organic layer was washed with water (100 ml) and dried ($MgSO_4$). The residue (32.5 g) was stirred with cyclohexane, the solid was filtered off, dissolved in warm cyclohexane, and the hot solution was decanted from the oil which separated on the flask, and cooled. The precipitated solid was filtered off, washed with cyclohexane and dried (8.9 g) (product A). The filtrate was combined with the previously separated oil, the mixture was evaporated in vacuo and the residue (19.25 g) was purified by column chromatography on silica gel (200 g) using a mixture of cyclohexane and benzene (10:1) as eluent, which afforded 1,2-bis(2-bromophenyl)ethylene (3.26 g, 21%) as a by-product. Change of the eluent to a mixture of cyclohexane and benzene (1:1) afforded an additional portion (6.70 g) of solid, which was identical with product A isolated above from the reaction mixture (cyclohexane), giving a total yield of 13.60 g (29%) of Z-(2-(2-bromophenyl)vinyl)-4-methyl-2-nitrobenzene.

TLC: $R_f$=0.75 ($SiO_2$: cyclohexane/ethyl acetate=5:1).

A solution of the above nitrobenzene (9.68 g, 30.3 mmol) in ethanol (110 ml) and methanol (40 ml) was hydrogenated 2 h at 3 MPa in the presence of morpholine (0.6 ml) and Rh/C (KO 319) catalyst (2 g). The catalyst was filtered off, the filtrate evaporated in vacuo and the residue was stripped with toluene (3×20 ml). The oily residue crystallized after standing at room temperature. After washing the solid with petroleum ether and drying, 2-(2-(2-bromophenyl)ethyl)-5-methylaniline (8.15 g, 92%) was obtained.

M.p. 67–69° C.

Calculated for $C_{15}H_{16}BrN$: C, 62.08%; H, 5.56%; Br, 27.54%; N, 4.83%; Found: C, 62.45%; H, 5.70%; Br, 27.25%; N, 5.06%.

A mixture of above amine (10.4 g, 0.036 mol) and sodium formate (4.9 g, 0.072 mol) in formic acid (70 ml) was heated at reflux temperature for 3 h and left to stand overnight. The reaction mixture was poured into water (500 ml) and stirred for 30 minutes. The solid was filtered off, washed with water and subsequently with ethanol. After drying in air, N-(2-(2-(2-bromophenyl)ethyl)-5-methylphenyl)formamide (8.3 g, 72%) was obtained.

M.p. 167–169° C.

A mixture of the above formyl derivative (6.50 g, 20 mmol), potassium carbonate (3.39 g, 24 mmol), copper (0.81 g, 13 mmol) and copper (I) bromide (1.02 g, 7 mmol) in dimethyl sulfoxide (40 ml) was heated to 160° C., cooled, 20% sodium hydroxide (4 ml) was added and the mixture was heated to 75° C. for 30 minutes. The mixture was poured into water (400 ml) and ethyl acetate (500 ml), the solid was filtered off, the organic layer was separated, washed with 1N hydrochloric acid, 10% sodium hydrogen carbonate and water (2×100 ml) and dried ($MgSO_4$). The residue (4.88 g) was purified by column chromatography on silica gel using a mixture of cyclohexane and benzene (1:1) as eluent. This afforded 2.26 g (54%) of 3-methyl-10,11-dihydro-5H-dibenzo[b,f]azepine.

TLC: $R_f$=0.75 ($SiO_2$: cyclohexane/ethyl acetate=5:1).

To a solution of the above azepine (2.09 g, 0.01 mol) in benzene (25 ml) a suspension of sodium amide (1.01 g, 0.013 mol, 50% suspension in toluene diluted with 5 ml of benzene) was added and the mixture was heated to 70° C. for 1.5 h under a nitrogen atmosphere. Then 1-tetrahydropyranyl-3-bromopropanol (2.90 g, 0.013 mol) was added and the mixture was heated to 70° C. for 19 h. After cooling, the reaction was quenched with water (20 ml), benzene was added (10 ml), the layers were separated and the organic layer was dried ($MgSO_4$). The residue (3.73 g) was dissolved in methanol (20 ml), 6 N hydrochloric acid (6 ml) was added and the mixture was heated at reflux temperature for 30 min. Then the methanol was evaporated in vacuo, the residue was treated with benzene (20 ml) and water (10 ml), the aqueous layer washed once more with benzene (10 ml) and the combined benzene extracts were dried ($MgSO_4$). The solvent was evaporated in vacuo and the residue (2.65 g) was purified by column chromatography on silica gel (50 g) using a mixture of benzene and ethyl acetate (10:1) as eluent. This afforded 1.83 g (68%) of 5-(3-hydroxypropyl)-3-methyl-10,11-dihydro-5H-dibenzo[b,f]azepine as an oil.

TLC: $R_f$=0.25 ($SiO_2$: chloroform).

To a solution of the above alcohol (1.70 g, 6.3 mmol) and triethylamine (1.9 g, 18 mmol) in benzene, (25 ml) a solution of methanesulfonyl chloride (0.91 g, 7.9 mmol) in benzene (8 ml) was added dropwise over 15 minutes at 18–20° C. under cooling on an ice bath. The reaction mixture was stirred at room temperature for 2 h. Separated triethylamine hydrochloride was filtered off, washed with benzene (15 ml), the combined benzene layers were washed with water (2×25 ml) followed by brine (20 ml) and dried ($MgSO_4$). After evaporation of the solvent in vacuo the oily methanesulfonate (2.07 g, 94%) was used in the next step without further purification.

TLC: $R_f$=0.50 ($SiO_2$: chloroform).

A mixture of the above methanesulfonate (2.07 g, 6 mmol), ethyl 2-(1-piperazinyl)-3-pyridinecarboxylate (1.41 g, 6 mmol), potassium iodide (1.00 g, 6 mmol) and potassium carbonate (2.49 g, 18 mmol) in 2-butanone (40 ml) was heated at reflux temperature for 7 h. The mixture was cooled, water (75 ml) and ether (75 ml) were added, the organic phase was washed with water (20 ml) and dried ($MgSO_4$). The solvent was removed in vacuo, affording the ethyl ester of the title compound (3.07 g) as an oil.

TLC: $R_f$=0.35 ($SiO_2$: ammonia saturated chloroform/ethanol=50:1).

To a solution of the above crude ester (2.90 g) in 2-propanol (15 ml) a solution of oxalic acid dihydrate (0.85 g) in 2-propanol (5 ml) was added, the mixture was gently warmed and then cooled. The separated salt was filtered off, washed with additional 2-propanol and ether and dried in vacuo affording 2.97 g (83%) of 2-(4-(3-(3-methyl-10,11-dihydro-5H-dibenzo-[b,f]azepin-5-yl)-1-propyl)-1-piperazinyl)-3-pyridine carboxylic acid ethyl ester oxalate.

From the above oxalate (2.85 g) the free ester (1.91 g) was liberated in a dichloromethane suspension with ammonium hydroxide and obtained as an oil.

To a solution of above ester (1.83 g, 3.8 mmol) in ethanol (22 ml), 20% sodium hydroxide (2.5 ml) was added and the mixture was stirred for 5 h at room temperature. The main portion of ethanol was removed in vacuo, the residue dissolved in dichloromethane (180 ml) and acidified with 2 N hydrochloric acid, the aqueous layer was separated, the organic layer was washed with water (10 ml), dried ($MgSO_4$) and the solvent was removed in vacuo. The foamy residue was evaporated with acetone (3×20 ml) and the amorphous solid (1.81 g ) was dissolved in acetone. The crystalline, in acetone insoluble title compound precipitated from the solution and was obtained by filtration. (1.26 g, 67%).

M.p. 200–206° C.

Calculated for $C_{28}H_{32}N_4O_2$, HCl: C, 68.21%; H, 6.75%; Cl, 7.19%; N, 11.36%; Found: C, 68.05%; H, 6.83%; Cl, 7.28%; N, 10.95%.

Example 21

6-(4-(3-(Dibenzo[d,g][1,3,6]dioxazocin-12-yl)-1-propyl)-piperazin-1-yl)-pyridine-2-carboxylic acid hydrochloride

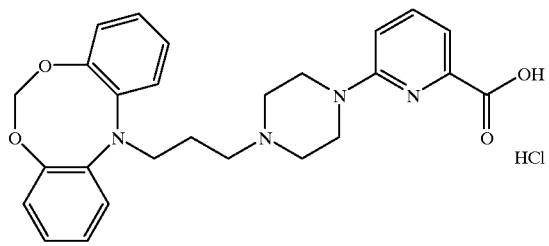

12H-Dibenzo[d,g][1,3,6]dioxazocine (1.7 g, 8 mmol, similarly prepared as described in EXAMPLE 3) was dissolved in dry benzene (25 ml) at 45° C. In a nitrogen atmosphere, a suspension of sodium amide in toluene (1.1 g, 50%, 14 mmol) was added and the mixture was stirred at 70° C. for 2.5 h. Freshly distilled 1-tetrahydropyranyloxy-3-bromopropane (2.88 g, 13 mmol, 72° C./70 Pa) was added and the mixture was heated at reflux temperature for 14 h and left overnight at room temperature. Benzene (25 ml) and water (25 ml) were added to the reaction mixture, stirred for 15 min and separated. The organic extract was dried (sodium sulfate) and the solvent evaporated in vacuo. The residue (4.9 g) was dissolved in methanol (20 ml), 6 N hydrochloric acid (6.7 ml, 40 mmol) was added, the mixture was stirred at 22° C. for 40 minutes and alkalised with 2 N sodium carbonate (20 ml). The product was extracted with benzene (80 ml), the organic phase washed with water (30 ml), dried (sodium sulfate) and evaporated in vacuo (3.5 g). The raw product was purified by chromatography on silica gel (80 g), using a mixture of benzene and ethylacetate (10:1) as eluent. 12-(3-Hydroxypropyl)dibenzo[d,g][1,3,6]dioxazocine (1.36 g, 47%) was obtained as an oil.

TLC: $R_f$=0.45 ($SiO_2$: benzene/ethyl acetate=10:1).

A solution of methanesulfonyl chloride (0.98 g, 8.6 mmol) in dry toluene (10 ml) was added dropwise to a stirred solution of the above propanol derivative (1.36 g, 5 mmol) and triethylamine (1.6 g, 15 mmol) in dry toluene (40 ml), under a nitrogen atmosphere, over 20 minutes at ambient temperature. A slightly exothermic reaction occurred. The reaction mixture was stirred at 24° C. for 3 h and then at 36° C. for 1.5 h. The reaction mixture was diluted with toluene (50 ml), washed with water (4×30 ml) and brine (25 ml), dried (sodium sulfate) and evaporated in vacuo. The oily mesylate (1.8 g, 100%) was used for the next step without further purification.

TLC: $R_f$=0.36 ($SiO_2$: benzene/ethyl acetate=10:1).

The above mesylate (1.8 g, 5 mmol), ethyl 6-(piperazin-1-yl)pyridine-2-carboxylate (1.9 g, 8 mmol), dry potassium carbonate (1.6 g, 12 mmol) and potassium iodide (0.15 g, 1 mmol) in dry acetone (30 ml) and N,N-dimethylformamide (10 ml) was stirred at reflux temperature for 5 h. Acetone was distilled off, the residue was dissolved in benzene (150 ml) and washed with water (4×50 ml) and brine (30 ml), dried (sodium sulfate) and evaporated in vacuo. The oily residue (3.54 g) was purified by chromatography on silica gel (70 g), using first benzene and then ethyl acetate as eluents). This provided the ethyl ester of the title compound (1.44 g, 59%) as an oil.

TLC: $R_f$=0.62 ($SiO_2$: benzene/ethyl acetate=10:1).

A solution of the above ethyl ester (1.44 g, 2.95 mmol) in ethanol (15 ml) and 5 N sodium hydroxide (20 ml) was stirred 15 minutes at 50–55° C. and then 21 h at 22° C., dichloromethane (200 ml) was added and the mixture was acidified to pH 1 with 2.5 N hydrochloric acid. The organic layer was separated, dried (sodium sulfate) and evaporated in vacuo to obtain 1.14 g of a solid residue, which was triturated with a mixture of acetone (15 ml) and ether (20 ml). The product was filtered off and washed with acetone-ether (2:3, 3×10 ml) and ether (5 ml) to yield 0.9 g (79%) of the title compound.

M.p. 224–227° C.

Calculated for $C_{26}H_{29}N_4O_4$, HCl, 0.5 $H_2O$: C, 61.71%; H, 5.98%; N, 11.07%; Found C, 61.60%; H, 6.05%; N, 10.79%.

What is claimed is:

1. A compound of formula I

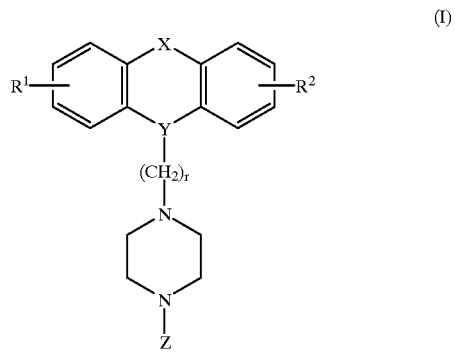

(I)

wherein $R^1$ and $R^2$ independently are hydrogen, halogen, trifluoromethyl, hydroxy, $C_{1-6}$-alkyl or $C_{1-6}$-alkoxy; and X is —$CH_2CH_2$—; and Y is >C̲H—$CH_2$— or >C̲=CH— wherein only the underscored atom participates in the ring system; and r is 1, 2 or 3; and Z is selected from

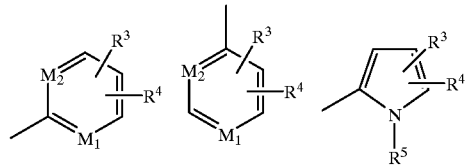

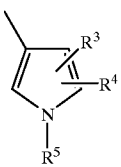

wherein $M_1$ is CH and $M_2$ is N, or $M_2$ is CH and $M_1$ is N, or $M_1$ and $M_2$ are both N;

$R^5$ is hydrogen, $C_{1-6}$-alkyl, phenyl or benzyl; and $R^3$ is hydrogen, halogen, trifluoromethyl, nitro or cyano; and $R^4$ is halogen, trifluoromethyl, nitro, cyano, $(CH_2)_mCOR^{11}$, $(CH_2)_mOH$ or $(CH_2)_mSO_2R^{11}$ wherein $R^{11}$ is hydroxy, $C_{1-6}$-alkoxy or $NHR^{12}$, wherein $R^{12}$ is hydrogen or $C_{1-6}$-alkyl; and m is 0, 1 or 2;

or a pharmaceutically acceptable salt thereof.

2. A compound according to claim 1 wherein $R^1$ and $R^2$ independently are hydrogen, halogen, trifluoromethyl or $C_{1-6}$-alkyl.

3. A compound according to claim 1 wherein r is 1 or 2.

4. A compound according claim 1 wherein Z is selected from

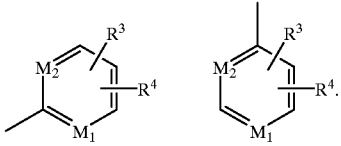

5. A compound according to claim 1 wherein $R^3$ is hydrogen, trifluoromethyl, nitro or cyano.

6. A compound according to claim 1 wherein $R^4$ is trifluoromethyl, nitro, cyano or $(CH_2)_mCOR^{11}$.

7. A compound according to claim 1 wherein m is 0 or 1.

8. A compound according to claim 1 wherein $R^{11}$ is hydroxy.

9. A compound according to claim 1 selected from the following:

2-(4-(3-(10,11-Dihydro-5H-dibenzo[a,d]cyclohepten-5-ylidene)-propyl)-1-piperazinyl)-3-pyridine-carboxylic acid;

1-(3-(10,11-Dihydro-5H-dibenzo[a,d]cyclohepten-5-ylidene)-1-propyl)-4-(3-trifluoromethyl-2-pyridyl) piperazine; and 6-(4-(3-(10,11-Dihydro-5H-dibenzo[a,d]cyclohepten-5-ylidene)-1-propyl)piperazin-1-yl)-2-pyridinecarboxylic acid;

or a pharmaceutically acceptable salt thereof.

10. A pharmaceutical composition comprising as an active component an effective amount of a compound according to claim 1 together with a pharmaceutically acceptable carrier or diluent.

11. The pharmaceutical composition according to claim 10 comprising between 0.5 mg and 1000 mg of the compound.

12. A method of treating neurogenic inflammation comprising administering to a subject in need thereof an effective amount of a compound according to claim 1.

13. A method of treating neurogenic inflammation comprising administering to a subject in need thereof a pharmaceutical composition according to claim 10.

14. A method of treating neurogenic inflammation associated with neuropathy, rheumatoid arthritis, migraine or itching comprising administering to a subject in need thereof an effective amount of a compound of claim 1.

15. A method of treating neurogenic inflammation associated with neuropathy, rheumatoid arthritis, migraine or itching comprising administering to a subject in need thereof a pharmaceutical composition of claim 10.

16. A method of treating insulin resistance in non-insulin-dependent diabetes mellitus (NIDDM) or aging-associated obesity comprising administering to a subject in need thereof an effective amount of a compound of claim 1.

17. A method of treating insulin resistance in non-insulin-dependent diabetes mellitus (NIDDM) or aging-associated obesity comprising administering to a subject in need thereof a pharmaceutical composition of claim 10.

18. A compound of formula I

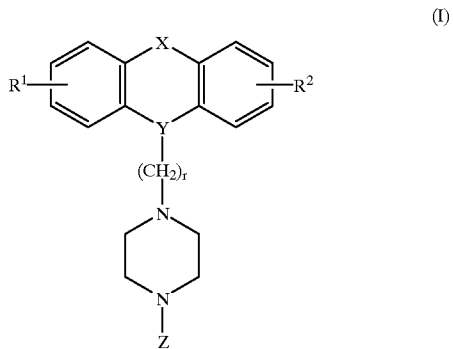

(I)

wherein $R^1$ and $R^2$ independently are hydrogen, halogen, trifluoromethyl, hydroxy, $C_{1-6}$-alkyl or $C_{1-6}$-alkoxy; and X is $-CH_2CH_2-$; and Y is $>\underline{C}H-CH_2-$ or $>\underline{C}=CH-$ wherein only the underscored atom participates in the ring system; and r is 1, 2 or 3; and Z is selected from

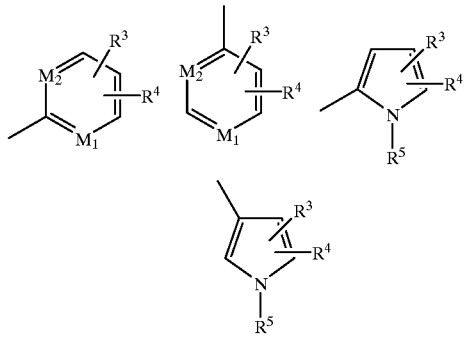

wherein $M_1$ and $M_2$ are both CH;

$R^5$ is hydrogen, $C_{1-6}$-alkyl, phenyl or benzyl; and $R^3$ is hydrogen, halogen, trifluoromethyl, nitro or cyano; and $R^4$ is halogen, trifluoromethyl, nitro, cyano, $(CH_2)_mCOR^{11}$, $(CH_2)_mOH$ or $(CH_2)_mSO_2R^{11}$ wherein $R^{11}$ is hydroxy, $C_{1-6}$-alkoxy or $NHR^{12}$, wherein $R^{12}$ is hydrogen or $C_{1-6}$-alkyl; and m is 0, 1 or 2;

or a pharmaceutically acceptable salt thereof.

19. A compound according to claim 18 selected from the following:

1-(3-(10,11-Dihydro-5H-dibenzo[a,d]cyclohepten-5-ylidene)-1-propyl)-4-(2-nitrophenyl)-piperazine;

2-(4-(3-(10,11-Dihydro-5H-dibenzo[a,d]cyclohepten-5-ylidene)-1-propyl)-1-piperazinyl)benzonitrile; and 2-(4-(3-(10,11-Dihydro-5H-dibenzo[a,d]cyclohepten-5-ylidene)-1-propyl)-1-piperazinyl)-benzoic acid;

or a pharmaceutically acceptable salt thereof.

20. A pharmaceutical composition comprising as an active component an effective amount of a compound according to claim 18 together with a pharmaceutically acceptable carrier or diluent.

21. The pharmaceutical composition according to claim 20 comprising between 0.5 mg and 1000 mg of the compound.

22. A method of treating neurogenic inflammation comprising administering to a subject in need thereof an effective amount of a compound according to claim 18.

23. A method of treating neurogenic inflammation comprising administering to a subject in need thereof a pharmaceutical composition according to claim 20.

24. A method of treating neurogenic inflammation associated with neuropathy, rheumatoid arthritis, migraine or itching comprising administering to a subject in need thereof an effective amount of a compound of claim 18.

25. A method of treating neurogenic inflammation associated with neuropathy, rheumatoid arthritis, migraine or itching comprising administering to a subject in need thereof a pharmaceutical composition of claim 20.

26. A method of treating insulin resistance in non-insulin-dependent diabetes mellitus (NIDDM) or ageing-associated obesity comprising administering to a subject in need thereof an effective amount of a compound of claim 18.

27. A method of treating insulin resistance in non-insulin-dependent diabetes mellitus (NIDDM) or ageing-associated obesity comprising administering to a subject in need thereof a pharmaceutical composition of claim 20.

* * * * *